(12) United States Patent
Boussaad et al.

(10) Patent No.: US 7,635,423 B2
(45) Date of Patent: *Dec. 22, 2009

(54) REDOX POTENTIAL MEDIATED, HETEROGENEOUS, CARBON NANOTUBE BIOSENSING

(75) Inventors: Salah Boussaad, Wilmington, DE (US); Bruce A. Diner, Chadds Ford, PA (US); Janine Fan, Hockessin, DE (US); Vsevolod Rostovtsev, Swarthmore, PA (US); Ajit Krishnan, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 498 days.

This patent is subject to a terminal disclaimer.

(21) Appl. No.: 11/241,515

(22) Filed: Sep. 30, 2005

(65) Prior Publication Data
US 2007/0278111 A1 Dec. 6, 2007

Related U.S. Application Data

(60) Provisional application No. 60/615,356, filed on Sep. 30, 2004.

(51) Int. Cl.
*G01N 33/50* (2006.01)
(52) U.S. Cl. .................. 205/777.5; 204/403.01; 977/920; 977/957; 435/25
(58) Field of Classification Search ........ 204/403.01; 205/777.5, 792; 435/4, 25; 977/920, 957, 977/958
See application file for complete search history.

(56) References Cited

U.S. PATENT DOCUMENTS

2004/0136866 A1 7/2004 Pontis et al.

FOREIGN PATENT DOCUMENTS

| DE | 101 18 200 A1 | 10/2002 |
|---|---|---|
| WO | WO 02/48701 A2 | 6/2002 |
| WO | WO 2004/034025 A2 | 4/2004 |

OTHER PUBLICATIONS

Z. Li et al., Sequence-Specific Label-Free DNA Sensors Based on Silicon Nanowires, Nano Letters, vol. 4(2):245-247, 2004.
Jong-In Hahm et al., Direct Ultrasensitive Electrical Detection of DNA and DNA Sequence Variations Using Nanowire Nanosensors, Nano Letters, vol. 4(1):51-54, 2004.
Philip G. Collins et al., Extreme Oxygen Sensitivity of Electronic Properties of Carbon Nanotubes, Science, vol. 287:1801-1804, 2000.
Jun Li et al., Carbon Nanotube Nanoelectrode Array for Ultrasensitive DNA Detection, Nano Letters, vol. 3(5):597-602, 2003.
Jing Kong et al., Nanotube Molecular Wires as Chemical Sensors, Science, vol. 287:622-625, 2000.
Besteman, Koen et al., Enzyme-Coated Carbon Nanotubes as Single-Molecule Biosensors, Nano Letters, 2003, pp. 727-730, vol. 3, No. 6, American Chemical Society.
Teh, Kwok-Siong et al., A Polypyrrole-Carbon-Nanotube (PPY-MWNT) Nanocomposite Glucose Sensor, IEEE International Conference on Micro Electro Mechanical Systems, Technical Digest, Jan. 2004, pp. 395-398.
International Search Report, International Application No. PCT/US05/35632, Dated Jun. 25, 2008.

*Primary Examiner*—Kaj K Olsen

(57) ABSTRACT

This invention relates to the field of nanotechnology. Specifically the invention describes a nanosensor for the detection of an analyte in which the redox potential in solution is altered thereby causing changes in carbon nanotube conductance.

35 Claims, 21 Drawing Sheets

A

B

Determination of dissociation constants for inhibitors

REDOX POTENTIAL MEDIATED, HETEROGENEOUS, CARBON NANOTUBE BIOSENSING

FIELD OF INVENTION

This invention relates to the field of nanotechnology. Specifically the invention describes a nanosensor for the detection of an analyte in which the redox potential of a redox effector in solution is altered thereby causing changes in carbon nanotube conductance.

BACKGROUND OF THE INVENTION

There is an increasing need for rapid, small scale and highly sensitive detection of biological molecules in medical, bioterrorism, food safety, and research applications. Nanostructures such as silicon nanowires and carbon nanotubes display physical and electronic properties amenable to use in miniature devices. Carbon nanotubes (CNTs) are rolled up graphene sheets having a diameter on the nanometer scale and typical lengths of up to several micrometers. CNTs can behave as semiconductors or metals depending on their chirality. Additionally, dissimilar carbon nanotubes may contact each other allowing the formation of a conductive path with interesting electrical, magnetic, nonlinear optical, thermal and mechanical properties.

It is known that single walled carbon nanotubes are sensitive to their chemical environment, specifically that exposure to air or oxygen alters their electrical properties (Collins et al. (2000) Science 287:1801). Additionally, exposure of CNTs to gas molecules such as $NO_2$ or $NH_3$ alters their electrical properties (Kong et al. (2000) Science 287:622). Thus chemical gas sensors can be designed, based on how they influence the electrical properties of carbon nanotubes such as described in DE10118200.

Detection of biomolecules has been achieved using probes that are attached to nanotubes or silicon nanowires. For example, a device using peptide nucleic acid receptors, designed to recognize a specific DNA sequence and attached to the surface of silicon nanowires, was able to detect the presence of a DNA sequence through hybridization-induced conductance changes (Hahm and Lieber (2003) Nano Lett. 4:51). Hybridization of a single stranded DNA probe attached to silicon nanowires with the complementary DNA strand was detected by conductance changes (Z. Li et al. (2003) Nano Lett. 4:245). In these two cases detection depends on the nanowires behaving as field effect transistors where changes in nanowire conductance result from binding of the target DNA to its complement, directly at the nanowire surface.

Hybridization of a single-stranded polyC DNA probe attached to carbon nanotubes with the complementary polyG DNA strand was detected amperometrically. (J. Li et al. (2003) Nano Lett. 3:597). In this case the oxidation of $Ru(bpy)_3^{2+}$ was mediated by the guanine bases of the DNA, attached by hybridization to the CNTs.

In WO 02/48701, articles are described that use nanowires, including CNTs, to detect different types of analytes including biological analytes. The nanowire may be modified by attaching an agent that is designed to bind an analyte, the binding to the nanowire or to a coating on the nanowire then causes a detectable change in conductance. In this detection system, the interaction between the binding agent and the analyte to be detected alters the electrical conductance of the nanowire. This requirement in turn limits the functional location of the binding agent with respect to the nanowire in that they must be in close proximity, 5 nanometers or less.

Carbon nanotubes have been used in electrocatalysis. Microelectrodes, constructed of multiwalled carbon nanotubes, were shown to provide a catalytic surface for electrochemical reduction of dissolved oxygen, potentially useful in fuel cell applications (Britto et al. (1999) Advanced Materials 11:154). A film of single walled carbon nanotubes functionalized with carboxylic acid groups on a glassy carbon electrode showed electrocatalytic behavior with several redox active biomolecules, involving reduction of the carboxylic acid groups (Luo et al. (2001) Anal. Chem. 73:915). Toluene-filled multiwalled carbon nanotubes as a film on a gold electrode surface were shown to respond better to electroactive biomolecules than empty carbon nanotubes (Zhang et al. (2003) Electrochimica Acta 49:715).

In WO 2004/034025, a system to measure the redox potential is described that uses a potentiometric electrochemical system based on a metal-coated silicon nanowire.

There is a need for a nanoscale detection system that does not require the binding of a binding agent and target analyte directly to the detecting nanowire or CNT. Applicants have solved this problem by developing a single-walled carbon nanotube nanosensor that responds to a target analyte by altering the redox potential in solution, which in turn alters the redox state of the CNT and causes a change in its conductance. In addition to expanding the possibility of binding agent-target analyte pairs that may be used in a nanoscale detection system, this novel system removes the spatial limitation for close proximity of the binding agent and CNT.

SUMMARY OF THE INVENTION

The present invention provides a nanosensor for the detection of an analyte. The nanosensor comprises an electrically conducting path of semiconducting single walled carbon nanotubes having a baseline conductance, in contact with an effector solution comprising a redox effector molecule. The effector solution has a given redox potential that is correlated to the redox state of the redox effector molecule. Modulations in the redox potential of the effector solution give rise to changes in the conductance of the CNT with respect to the baseline conductance. The nanosensor additionally comprises a redox reporter that interacts with a redox active substrate and co-substrate. In the presence of an analyte the reporter interacts with the substrate and co-substrate oxidizing one and reducing the other altering the redox potential of the effector solution.

In one embodiment the redox reporter is incorporated into a redox reporter conjugate comprising the reporter linked to an analyte receptor that serves to bind the analyte. The analyte is captured on a support through a capture moiety, allowing interaction between the redox reporter or redox reporter conjugate to interact with the analyte.

In a second embodiment, a capture moiety on a surface captures a redox catalytic analyte, the presence of which is detected by the action of the analyte with a redox active substrate and co-substrate which affects the redox potential of the effector solution.

In a third embodiment, a redox reporter is attached to a surface and the action of the redox reporter with a redox active analyte and co-substrate affects the redox potential of the effector solution.

Optionally the nanosensor may comprise a redox mediator. The mediator functions to facilitate the transfer of electrons from a reduced moiety (substrate or co-substrate) to the effector solution surrounding the carbon nanotube.

Accordingly the invention provides a nanosensor for detecting the presence of an analyte comprising:
  a) at least two electrodes connected by an electrically conducting path comprised of one or more carbon nanotubes wherein at least one of said carbon nanotubes is semiconducting and wherein the carbon nanotube is in contact with an effector solution having a redox potential;
  b) a capture moiety having affinity for an analyte and attached to a surface;
  c) a redox reporter conjugate comprising a redox reporter linked to an analyte receptor, said analyte receptor having affinity for the analyte; and
  d) a redox active substrate and a co-substrate.

In an alternate embodiment the invention provides a nanosensor for detecting the presence of a redox catalytic analyte comprising:
  a) at least two electrodes connected by an electrically conducting path comprised of one or more carbon nanotubes wherein at least one of said carbon nanotubes is semiconducting and wherein the carbon nanotube is in contact with an effector solution having a redox potential;
  b) a capture moiety having affinity for a redox catalytic analyte analyte and attached to a surface; and
  c) a redox active substrate and a co-substrate.

In another embodiment the invention provides a nanosensor for detecting the presence of a redox active analyte comprising:
  a) at least two electrodes connected by an electrically conducting path comprised of one or more carbon nanotubes wherein at least one of said carbon nanotubes is semiconducting and wherein the carbon nanotube is in contact with an effector solution having a redox potential; and
  b) a redox active analyte attached to a surface.

In a similar embodiment the invention provides a nanosensor for detecting the presence of an analyte comprising:
  a) at least two electrodes connected by an electrically conducting path comprised of one or more carbon nanotubes wherein at least one of said carbon nanotubes is semiconducting and wherein the carbon nanotube is in contact with a solution having an effector at a redox potential,
  b) a redox catalyst comprising an inhibitor whereby the catalytic activity of the catalyst is inhibited and an analyte receptor; and
  c) a redox active substrate and a co-substrate.

In one embodiment the invention provides a method for detecting an analyte comprising:
  a) providing a nanosensor comprising:
    i) at least two electrodes connected by an electrically conducting path comprised of one or more carbon nanotubes wherein at least one of said carbon nanotubes is semiconducting, and wherein the carbon nanotube is in contact with an effector solution having a redox potential wherein the carbon nanotube has a baseline conductance;
    ii) a capture moiety having affinity for an analyte, the capture moiety attached to a surface; and
    iii) a redox reporter conjugate comprising an analyte receptor and a redox reporter;
  b) providing a sample suspected of containing an analyte;
  c) contacting the sample of (b) with the capture moiety of the nanosensor of (a) wherein the analyte present in the sample binds to the capture moiety and the analyte receptor of the redox reporter conjugate to form a capture-analyte-redox reporter complex;
  d) contacting the capture-analyte-redox reporter complex of step (c) with a redox active substrate and co-substrate wherein the redox potential of the effector solution is altered resulting in a change in the conductance of the carbon nanotube with respect to the baseline conductance; and
  e) measuring the change in the conductance of the carbon nanotube with respect to the baseline conductance whereby the presence of the analyte is detected.

Alternatively the invention provides a method for detecting a redox catalytic analyte, comprising:
  a) providing a nanosensor comprising:
    i) at least two electrodes connected by an electrically conducting path comprised of one or more carbon nanotubes wherein at least one of said carbon nanotubes is semiconducting, and wherein the carbon nanotube is in contact with an effector solution having a redox potential and has a baseline conductance; and
    ii) a capture moiety having affinity for a redox catalytic analyte, the capture moiety attached to a surface;
  b) providing a sample suspected of containing an a redox catalytic analyte;
  c) contacting the sample of (b) with the capture moiety of the nanosensor of (a) wherein the a redox catalytic analyte, present in the sample binds to the capture moiety to form a capture-analyte complex;
  d) contacting the capture-analyte complex of step (c) with a redox substrate and co-substrate wherein the redox potential of the effector solution is altered resulting in a change in the conductance of the carbon nanotube with respect to the baseline conductance; and
  e) measuring the change in the conductance of the carbon nanotube with respect to the baseline conductance whereby the presence of the a redox catalytic analyte, is detected.

Similarly the invention provides a method for detecting a redox active analyte comprising:
  a) providing a nanosensor comprising:
    i) at least two electrodes connected by an electrically conducting path comprised of one or more carbon nanotubes wherein at least one of said carbon nanotubes is semiconducting, and wherein the carbon nanotube is in contact with an effector solution having a redox potential and has a baseline conductance; and
    ii) a redox reporter having a redox active analyte substrate and being attached to a surface;
  b) providing a sample suspected of containing a redox active analyte and a co-substrate wherein the redox potential of the effector solution is altered resulting in a change in the conductance of the carbon nanotube with respect to the baseline conductance; and
  c) measuring the change in the conductance of the carbon nanotube with respect to the baseline conductance whereby the presence of the redox active analyte is detected.

In another embodiment the invention provides a method for detecting an analyte comprising:
  a) providing a nanosensor comprising:
    i) at least two electrodes connected by an electrically conducting path comprised of one or more carbon nanotubes wherein at least one of said carbon nanotubes is semiconducting, and wherein the carbon nanotube is in contact with a solution having an effector at a redox potential and has a baseline conductance; and ii) a redox catalyst comprising an inhibitor whereby the catalytic activity of the catalyst is inhibited and an analyte receptor having affinity for an analyte;

b) providing a sample suspected of containing an analyte;

c) contacting the sample of (b) with the inhibited redox catalyst of (a) wherein the analyte binds to the analyte receptor displacing the inhibitor and activating the redox catalyst resulting in an alteration in the redox potential of the effector solution and a change in the conductance of the carbon nanotube; and d) measuring the change in the conductance of the carbon nanotube whereby the presence of the analyte is detected.

BRIEF DESCRIPTION OF THE FIGURES AND SEQUENCES

The invention can be more fully understood from the following detailed description and the accompanying sequence descriptions, which form a part of this application.

The sequence descriptions and content of the sequence listing attached hereto (additionally provided in a computer readable form) are incorporated by reference as a part of this application. The Sequences and Sequence Listing comply with the rules governing nucleotide and/or amino acid sequence disclosures in patent applications as set forth in 37 C.F.R. §1.821-1.825 ("Requirements for Patent Applications Containing Nucleotide Sequences and/or Amino Acid Sequence Disclosures—The Sequence Rules") and consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The Sequence Descriptions contain the one letter code for nucleotide sequence characters and the three letter codes for amino acids as defined in conformity with the IUPAC-IYUB standards described in *Nucleic Acids Research* 13:3021-3030 (1985) and in the *Biochemical Journal* 219 (No. 2):345-373 (1984) which are herein incorporated by reference. The symbols and format used for nucleotide and amino acid sequence data comply with the rules set forth in 37 C.F.R. §1.822.

SEQ ID NO:1 is oligo 27 and oligo 28 with sequence derived from the LDLR gene.

SEQ ID NO:2 is oligo 29 with sequence complementary to SEQ ID NO:1.

SEQ ID NO:3 is oligo 51 and oligo 53.

SEQ ID NO:4 is oligo 52.

SEQ ID NO:5 is oligo 50 and oligo 54.

SEQ ID NO:6 is oligo 32.

SEQ ID NO:7 is oligo 61.

FIG. 1 is a diagram of a nanosensor embodiment that includes a redox reporter conjugate bound to an analyte that is itself bound to a capture moiety on a surface. FIG. 1A shows a nanosensor comprising two electrodes connected by an electrically conducting path comprising at least one semiconducting carbon nanotube. FIG. 1B shows binding of an analyte to a capture moiety of the nanosensor to form an analyte-capture complex. FIG, 1C shows binding of a reporter conjugate to the analyte-capture complex to form a capture-analyte-redox reporter complex.

FIG. 2 is a diagram of a nanosensor embodiment where the analyte is itself a redox reporter able to react with a redox-active substrate and co-substrate, the redox potential of one of which is preferentially sensed by the nanotubes. FIG. 2A shows a nanosensor as in FIG. 1, with the format of the nanosensor modified to accommodate the addition of a redox catalytic analyte, typically an enzyme. FIG. 2B shows binding interaction of a redox active substrate and co-substrate that are with the bound redox catalytic analyte.

Figure 14:
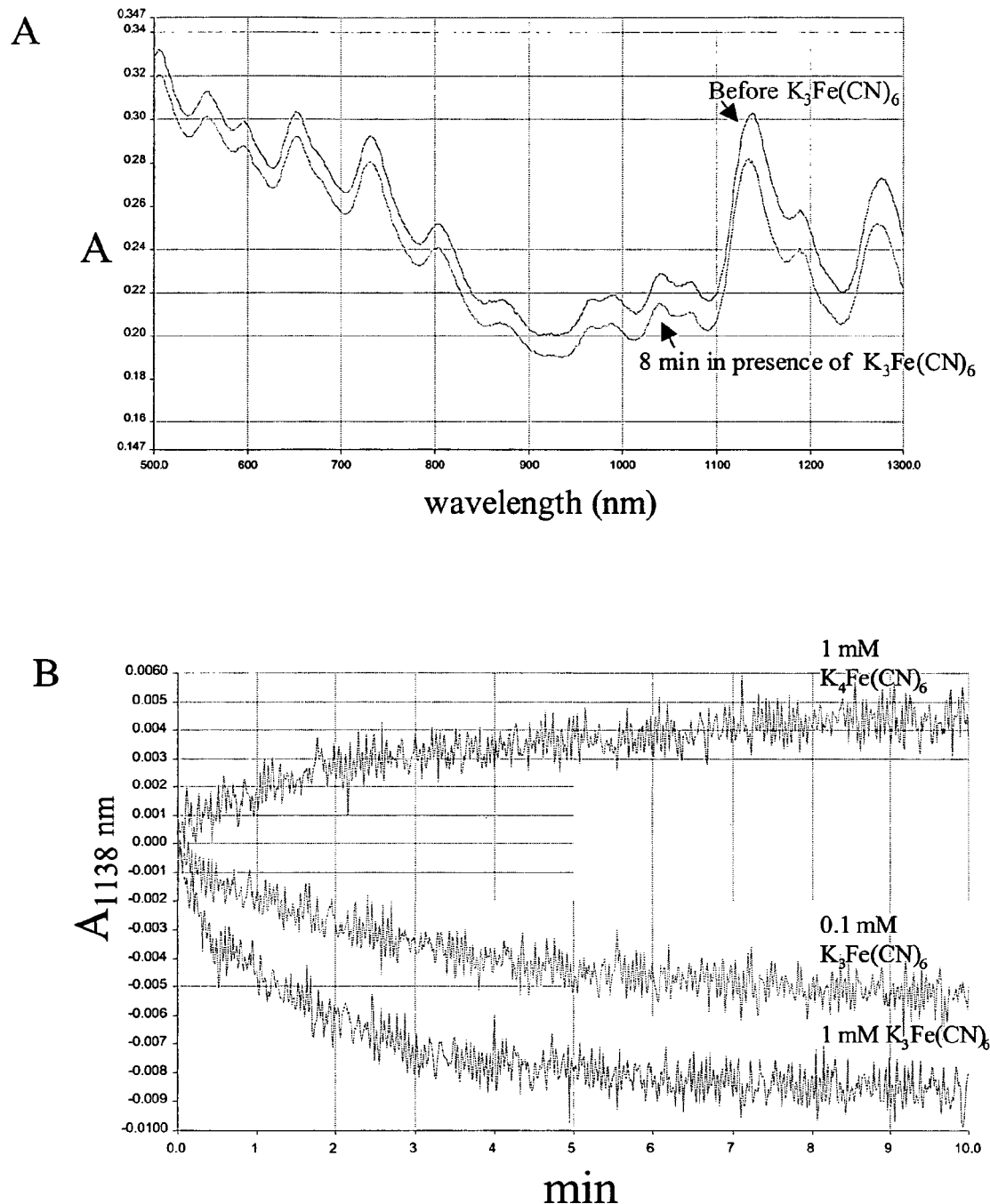

FIG. 14 shows (A) a spectrum of HiPco carbon nanotubes before and 8 min after the addition of 1 mM $K_3Fe(CN)_6$; (B) a time course of the evolution of the absorption at 1138 nm of surfactant dispersed HiPco carbon nanotubes following the addition of 0.1 and 1.0 mM $K_3Fe(CN)_6$ and 1 mM $K_4Fe(CN)_6$.

Figure 15:
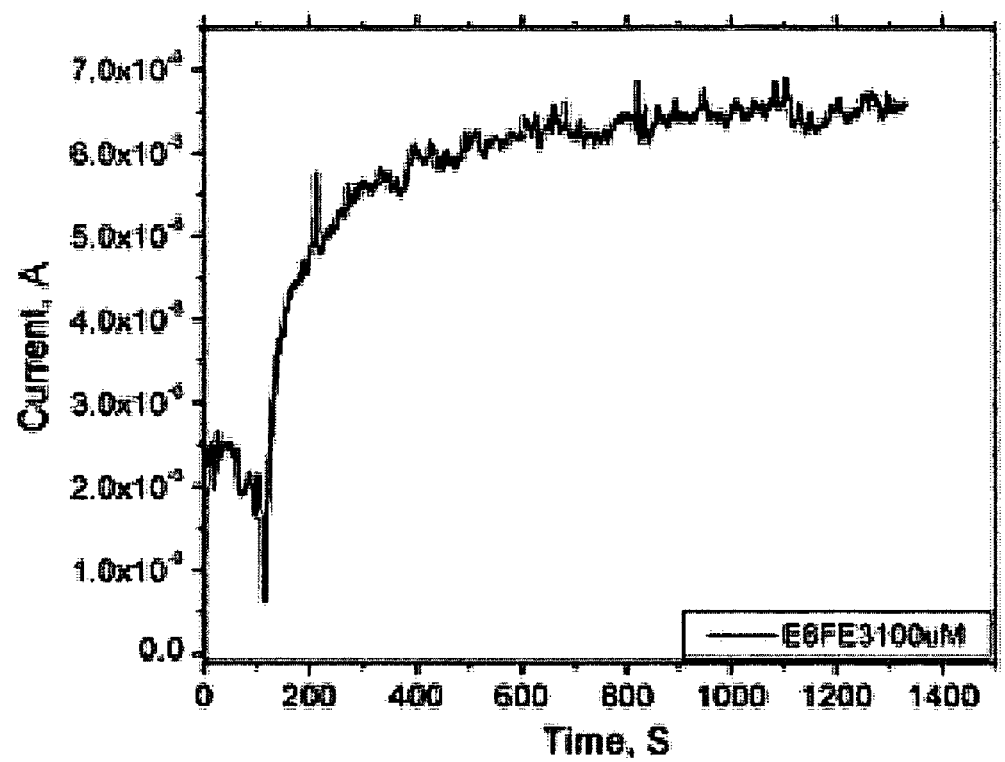

FIG. 15 shows a time course of the evolution of the conductance of CVD grown carbon nanotubes following the addition of 0.1 mM $K_3Fe(CN)_6$. Vsd=50 mV, Vg=−0.2 V.

Figure 16:
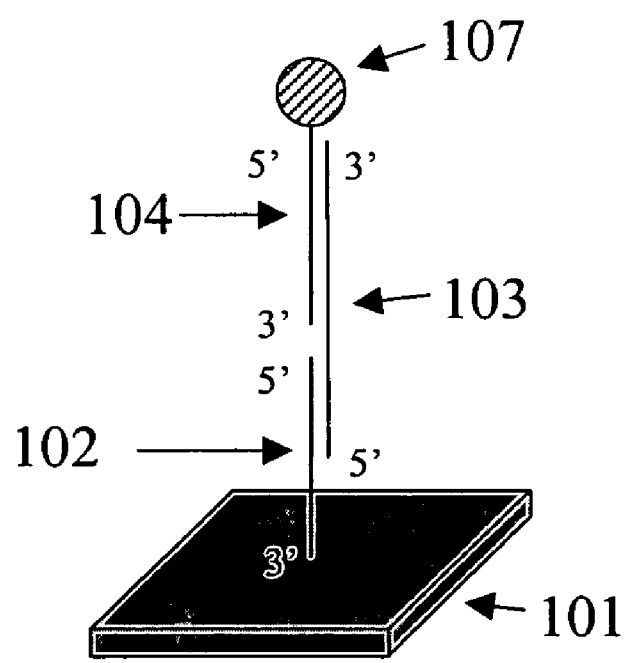

FIG. 16 is a diagram of hybridization between a surface attached oligonucleotide probe, a nucleic acid analyte, and a different oligonucleotide probe attached to laccase.

Figure 17:
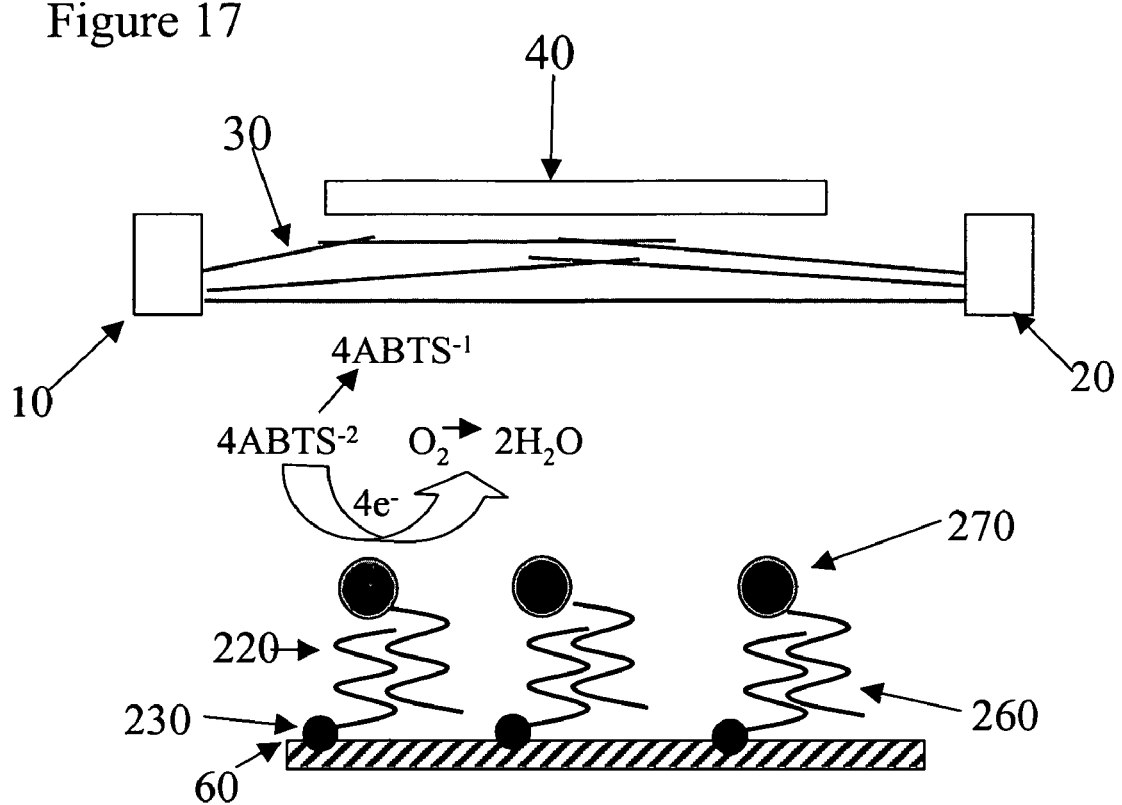

FIG. 17 is a diagram of CNT sensing as tested in Example 11.

Figure 18:
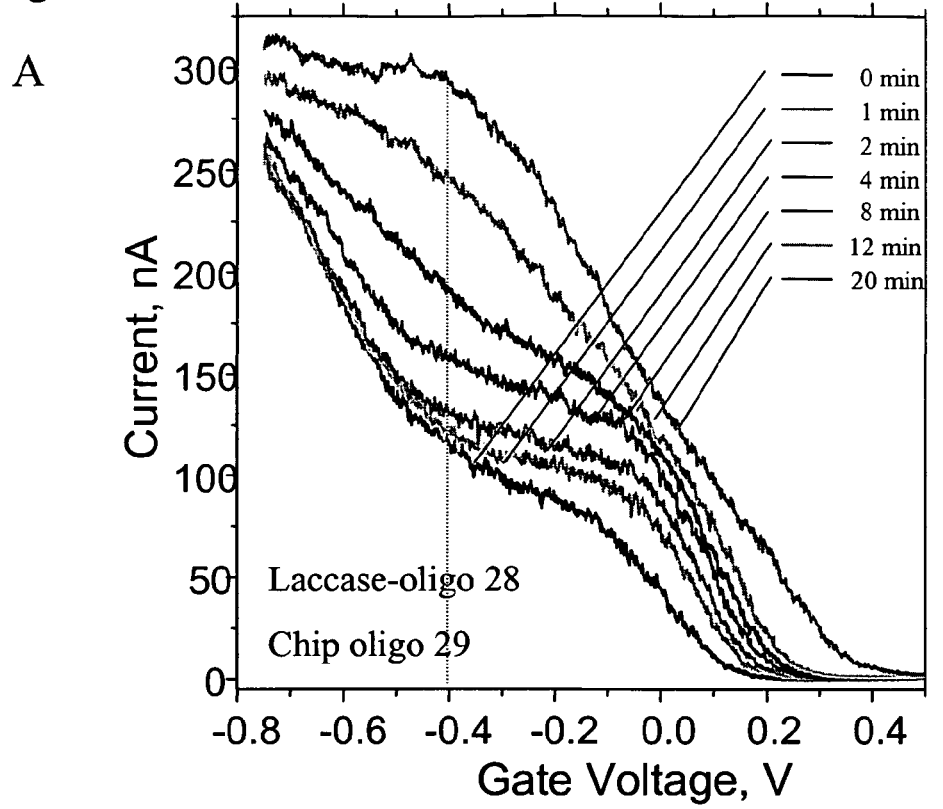
Figure 18:
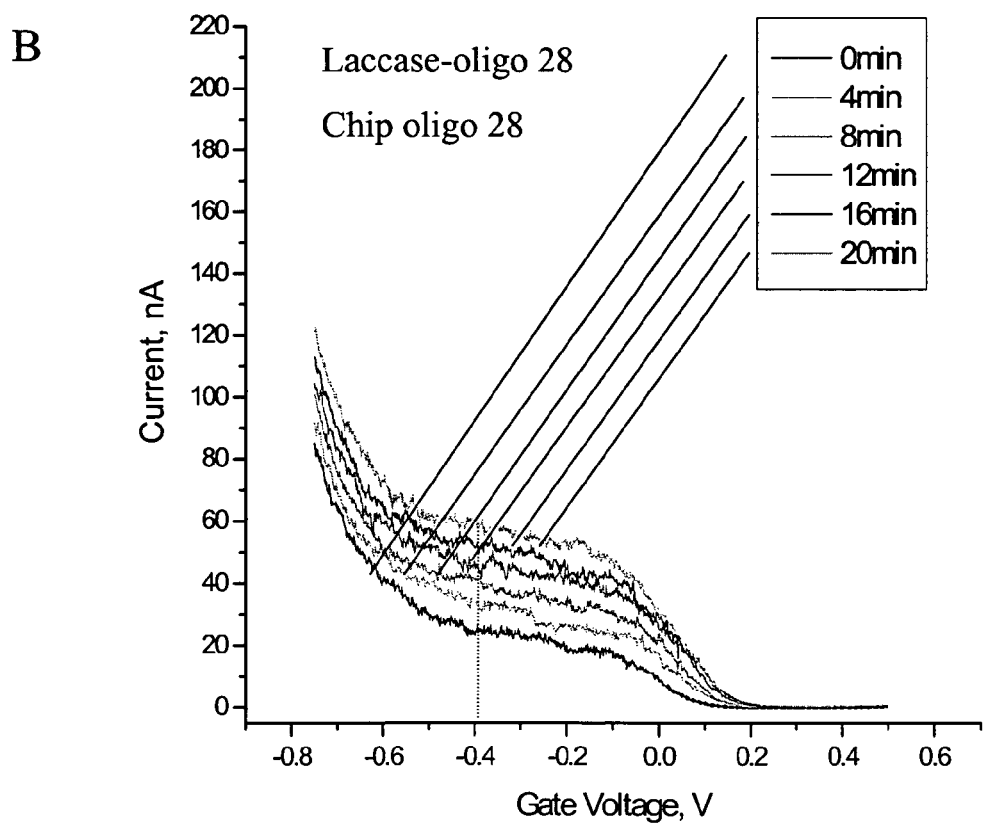

FIG. 18 shows the current vs gate voltage characteristics of a single-walled carbon nanotube device where a surface-attached oligo is either complementary (A) or non-complementary (B) to an oligo attached to laccase.

Figure 19:
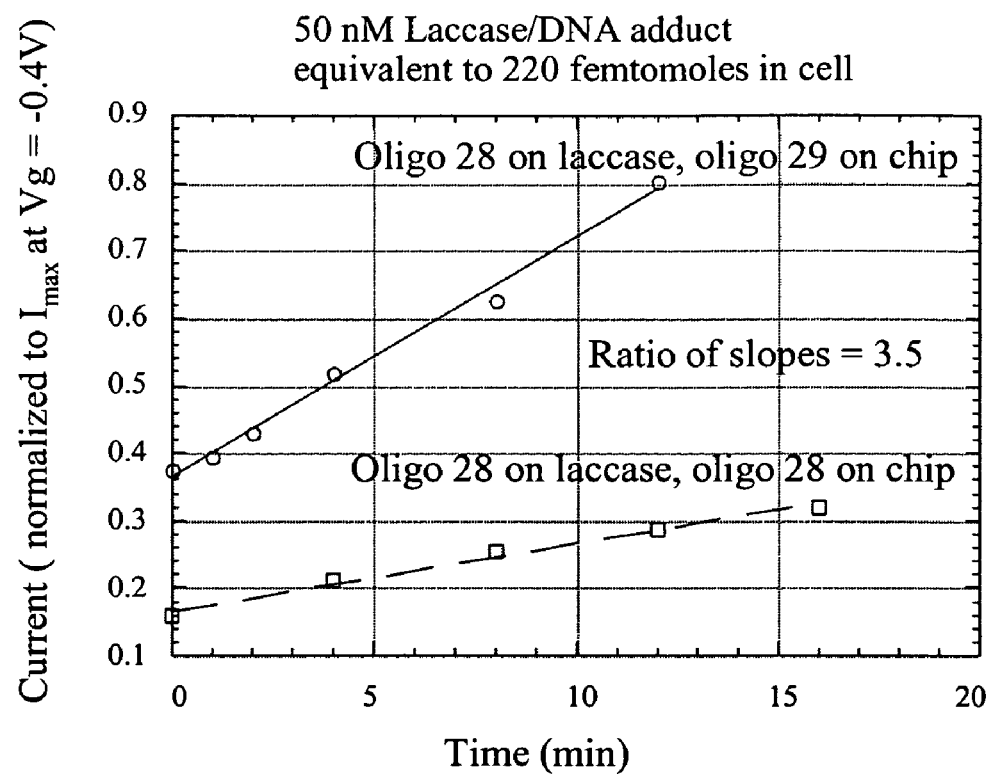

FIG. 19 shows plots of the change in current with time at a gate voltage, Vg of −0.4 V for the two experiments shown in FIG. 19.

Figure 20:
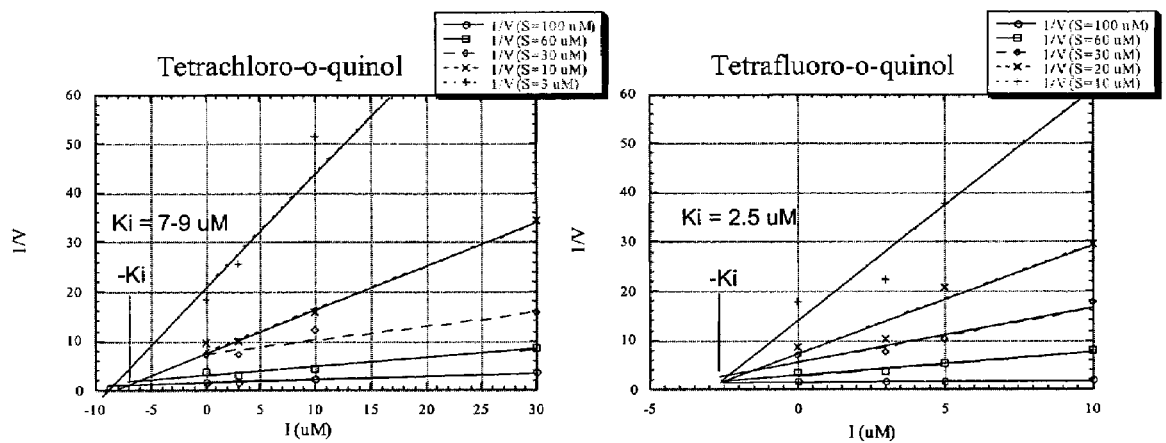

FIG. 20 plots the rate of $ABTS^{-2}$ oxidation with varying inhibitor concentration for (A) tetrachloro-o-quinol and (B) tetrafloro-o-quinol.

DETAILED DESCRIPTION

The present invention provides nanosensors for detecting analytes and methods for their use. The main elements of the nanosensor of the invention are:

An electrically conducting path between at least two electrodes comprised of at least one semiconducting CNT where the CNT has a baseline conductance;

An effector solution in contact with the CNT where the effector solution establishes a redox potential around the CNT;

A redox reporter, typically a catalyst, that oxidizes or reduces a redox substrate at the expense of a co-substrate; and A capture moiety, attached to a surface where the capture moiety binds the analyte. Optionally, the capture moiety may be the redox reporter.

Several advantages of this detection system are 1) the analyte or capture moiety-analyte complex itself does not need to directly change the conductance of the CNT; 2) the capture moiety does not need to be attached to or be in close proximity to the CNT; and, where the reporter is an enzyme; 3) the signal is greatly amplified through the turnover of the redox reporter.

The present invention also provides a method for detecting an analyte indirectly by first binding the analyte to a capture moiety that is attached to a surface, binding a redox reporter conjugate to the bound analyte, which acts upon a redox-active substrate and co-substrate. The change in redox potential of one of the substrates, acting as the redox effector or of a redox mediator, in equilibrium with one of the substrates, and acting as the effector, is measured as a change in conductance of at least one semiconducting CNT in a conductive path in contact with the solution. Another embodied method is to bind an analyte that is redox active to a capture moiety. In the presence of a redox active substrate and a redox active co-substrate, one of which acts as the effector or alters the redox potential of a redox mediator which acts as the effector, a change in the redox potential of the effector is detected via a change in the conductance of at least one semiconducting CNT in a conductive path in contact with the solution. An additional method for detecting an analyte indirectly is to allow an analyte that is a redox active substrate to react with a surface attached redox reporter in the presence of a co-substrate. One of the substrates, or a redox mediator in equilibrium with one of them, acts as the effector, the change in redox potential of which causes a change in the conductance of at least one semiconducting CNT in a conductive path in contact with the solution.

Highly sensitive nanoscale detection of biomolecules has utility in bioterrorism, biomedical, environmental, food safety, research, and other applications. Use of the present system wherein detection by the CNTs is of a change in redox potential in solution increases the diversity of biomolecules that may be assayed and the sensitivity of detection. Samples may be screened to detect a target biomolecule that would indicate the presence of a bioterrorism agent, a disease agent, a genetic disorder, an environmental contaminant, a food pathogen, a desired product, and other such components.

The following definitions and abbreviations are to be used for the interpretation of the claims and the specification.

"CNT" means carbon nanotube.

"$ABTS^{-2}$" refers to 2,2'Azino-di-(3-ethylbenzthiazoline-sulfonate)

The term "nanotube" refers to a single-walled hollow cylinder having a diameter on the nanometer scale and a length of several micrometers, where the ratio of the length to the diameter, i.e., the aspect ratio, is at least 5. In general, the aspect ratio is between 100 and 100,000.

By "carbon-based nanotube" or "carbon nanotube" herein is meant a single walled hollow cylinder composed primarily of carbon atoms.

The term "baseline conductance" refers to conductance measured prior to the addition of the sample or at the earliest time following the addition of a solution potentially containing the analyte for detection. The baseline conductance provides a measurement that can be compared to the conductance measurement made when the analyte is being detected.

The term "heterogeneous", as used in conjunction with the nanosenor and methods of the invention, refers to a sensor or method that makes use of reagent bound to a surface, typically a support. "Heterogeneous" is used antithetically to "homogeneous", where reagents are not bound to a surface. The term "heterogeneous catalysis" refers to catalysis in which the catalytic moiety is attached to a surface either directly or indirectly.

The term "analyte" or "target analyte" means the substance that is the object of detection by the nanosensor. Analytes may be a variety of materials and substances but are typically biomolecules and the product of biological reactions and events. A "redox catalytic analyte" for example is an analyte that has a catalytic function that has the potential of altering the redox potential of a solution. Redox catalytic analytes are often enzymes. Alternatively a "redox active analyte" is an analyte that may directly affect the redox potential of a solution.

The term "target biomolecule" refers to a substance to be detected in a biological sample, or sample potentially containing biological material. The target biomolecule is an analyte that is part of a sample.

The term "capture moiety" refers to a molecule that can interact with and trap a target analyte. When a capture moiety is attached to a surface, the analyte bound to the capture moiety will be attached to the surface as well, such that it will not be removed during a wash step.

The term "reporter" or "redox reporter" will mean a catalytic substance capable of reacting with a substrate and co-substrate to alter the redox potential of the effector solution. The redox reporter may be chemically or catalytically based. Typical redox reporters of the invention are enzymes such as glucose oxidase that interact with a substrate (glucose) and a co-substrate (oxygen).

The term "redox reporter conjugate" refers to a molecule with dual functionality. The redox reporter conjugate is generally comprised of a reporter moiety (generally an enzyme or substance having catalytic activity) and an "analyte receptor". For the purposes of the present invention the "analyte receptor" will refer to that portion of the redox reporter conjugate that has specific affinity for the analyte.

The term "redox active substrate" and "redox active co-substrate" or "co-substrate" refer to substrates of the redox reporter or redox catalytic analyte. The reaction of the redox-active substrate with a redox-active co-substrate is catalyzed by a redox catalyst. In this case, one of the two substrates is oxidized and the other reduced.

The term "effector" or "redox effector" refers to a molecule in the effector solution that is in redox equilibrium with the carbon nanotubes. The redox effector may be directly the redox substrate or co-substrate or alternatively may be in redox equilibrium with the substrate or co-substrate and is oxidized or reduced by one of them.

The term "redox mediator" refers to a redox molecule whose redox potential is in equilibrium with the redox state of a redox active substrate and which, as an effector, causes a change in the CNT conductance.

The term "redox potential" refers to an electrochemical potential characterized by the log of the ratio of the concentrations of the oxidized to the reduced forms of a redox molecule, according to the Nernst equation.

The term "effector solution" means the solution comprising the "effector molecule" that is in contact with the CNT comprised within the nanosensor of the invention.

The term "charge carrier" refers to any molecule or other discrete entity that has the ability to receive or donate electrons and carry a charge.

The term "support" refers to any material comprised within the nanosensor that will serve as a support for the various elements of the sensor, including, but not limited to the CNTs, the capture moiety, the reporter conjugate and the analyte. Supports may take a variety of shapes and are composed of a variety of type of materials including polymers, matrices and gels.

The term "surface" refers to the exterior portion of any material. In the context of the present invention a surface will often be located at the solid-liquid interface.

The term "pad" refers to an area of a surface on a support that is a localized area for attachment of the capture moiety. The pad and the rest of the support may each be treated differently so that the pad is prepared for attachment of the capture moiety, and the capture moiety does not attach to the rest of the support.

The term "stamp" refers to a separate support from that on which the carbon nanotubes are placed. The capture moiety may be attached to the stamp surface, or to a portion of the stamp surface.

The term "attach" refers to the affixing to, specifically the affixing of a molecule to a surface such that the attached molecule is not removed from the surface under conditions of the detection process of the invention. Attachment may be directly between the molecule and the surface, or it may be indirectly through an attachment group or secondary attachment molecule.

As used herein the term "source electrode" will mean one of the three terminals of a field effect transistor from which the majority carrier flows into the transistor.

As used herein the term "drain electrode will mean one of the three terminals of a field effect transistor through which the majority carrier exits the transistor.

As used herein the term "gate electrode" will mean one of the three terminals of a field effect transistor which by means of an electric field controls the flow of charge carriers in the transistor, thereby controlling the output current.

The term "bound" refers to an interaction between two molecules to form a complex. The binding of a first molecule, which is attached to a surface, to a second molecule in solution captures the second molecule so that it is no longer free in solution.

The term "complex" refers to a group of two or more molecules that are bound to each other. Each molecule need not be bound to all other molecules in the complex, but each molecule is bound to at least one of the other molecules such that the group of molecules is held together. Accordingly a "capture-analyte-redox reporter complex" is a complex formed between an analyte, immobilized to a surface through the capture moiety and the elements of the reporter conjugate, i.e a reporter and an analyte receptor.

The term "binding partner" refers to one of two molecules that are able to interact with each other such that they form a complex. A "binding pair" consists of two binding partners. Binding pairs particularly suitable in the present invention include, but are not limited to the pair combinations of antigen/epitope, receptor/ligand, binding protein/protein, nucleic acid binding polypeptide/nucleic acid, complementary nucleic acid single strands and peptide nucleic acid and complementary nucleic acid.

The term "polypeptide" refers to a chain of amino acids that may be an entire protein or may be a portion thereof. Polypeptides may be natural or synthetic, and may include one or more artificial chemical analogues of a naturally occurring amino acid. For the purposes of this description a peptide is considered to be a type of polypeptide and a polypeptide is a type of protein.

The term "antibody" refers to a protein or glycoprotein encoded by an immunoglobulin gene, or portion thereof. Any portion of a natural antibody which is able to bind to its antigen, called immunoreactive fragment", is included in the term antibody. The antibody may be monoclonal or polyclonal. Though natural antibodies are tetramers of two heavy and two light chains, a single heavy and light chain may be adequate for antigen binding, as in single chain antibodies. The variable regions of the light and heavy chains are generally the antigen recognition regions of an antibody. Thus a single variable light chain and a single variable heavy chain may suffice for antigen binding, and these may be joined together directly or through a peptide linker.

An "oligonucleotide" or "oligo" is a polymer of RNA, DNA, or peptide nucleic acid (PNA). It optionally contains synthetic, non-natural or altered nucleotide bases. The base sequence of an oligonucleotide probe is complementary to the sequence of the portion of the target nucleic acid molecule to which hybridization is desired. An oligonucleotide probe may also be used to bind to a nucleic acid binding protein. In this case, it may be double-stranded if interaction with the binding protein requires a double-strand structure. An oligonucleotide may also be covalently linked to a protein.

The term "peptide nucleic acids" refers to a material having nucleotides coupled together by peptide linkers.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein. The conditions of temperature and ionic strength determine the "stringency" of the hybridization. Stringency conditions can be adjusted to screen for moderately similar fragments, such as homologous sequences from distantly-related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater is the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., *supra,* 9.50-9.51). For hybridizations with shorter nucleic acids, i.e., oligonucleotides, the position of mismatches becomes more important, and the length of the oligonucleotide determines its specificity (see Sambrook et al., *supra,* 11.7-11.8).

Nanosensors

The nanosensor of the invention involves a heterogeneous reporting system for the detection of an analyte. Typically the nanosensor comprises the following elements:

An electrical conducting path between at least two electrodes comprised of at least one semiconducting CNT where the CNT maintains a baseline conductance;

An effector solution in contact with the CNT where the effector solution establishes a redox potential around the CNT; and A redox reporter, typically a catalyst, that oxidizes or reduces a redox substrate at the expense of a co-substrate; and A capture moiety, attached to a surface where the capture moiety binds the analyte. In some variations of the sensing format, and depending on the nature of the analyte to be detected, the analyte may not require immobilization via a capture moiety but will be detected via its interaction with an immobilized reporter.

Figure 1:
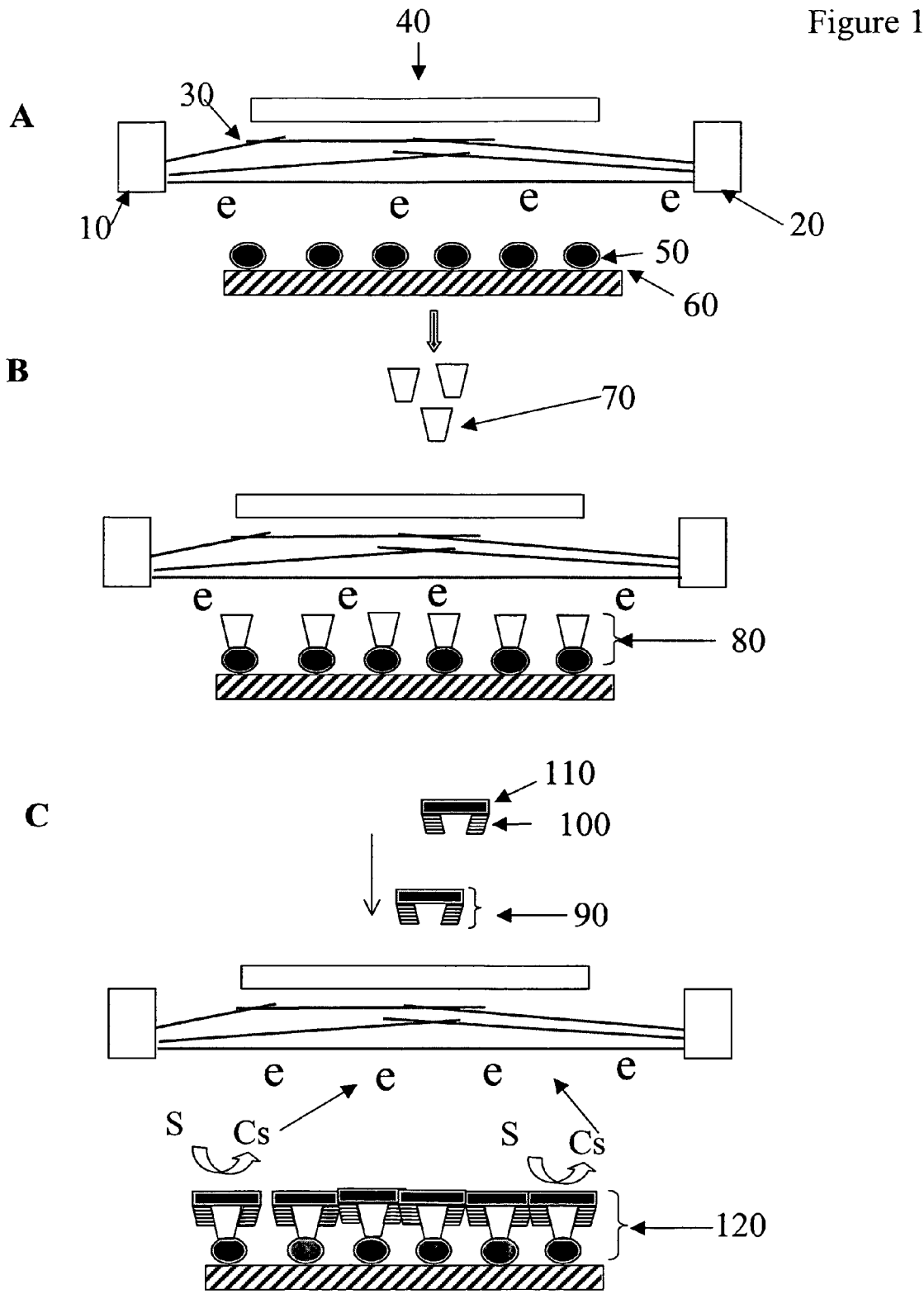

The invention may best be understood by making reference to the diagrams. The nanosensor of the invention may be used in a variety of formats depending on the nature of the analyte to be detected. For example, one embodiment is shown in FIG. 1. Referring to FIG. 1A, the nanosensor comprises two electrodes (10, 20) connected by an electrically conducting path comprising at least one semiconducting carbon nanotube (CNT)(30). The CNT (30) inherently possesses a baseline conductance. The electrodes (10, 20) may be independently either source or drain. The CNT (30) is in association with an effector solution (e) which has a redox potential. The nanosensor additionally may comprise a gate electrode (40) which generates an electric field to gate the conductance of the CNT. The nanosensor additionally comprises a surface (60) having a capture moiety (50) attached thereto. As shown in FIG. 1B, introduction of an analyte (70) to the nanosensor results in the binding of the analyte (70) to the capture moiety (50) to form an analyte-capture complex (80). As illustrated in FIG. 1C, the addition of a reporter conjugate (90) comprising a reporter element (110) and an analyte receptor (100) results in the binding of the reporter conjugate (90) to the analyte-capture complex (80) to form a capture-analyte-redox reporter complex (120). Introduction of a redox active substrate (S) and a co-substrate (Cs) results in the oxidation of the substrate (S) and the reduction of the co-substrate (Cs) (or vice versa) producing an alteration of the redox potential of the effector solution. Changes in the redox potential of the effector solution produce a corresponding change in the conductance of the CNT which can be measured to determine the presence of the analyte.

Figure 2:
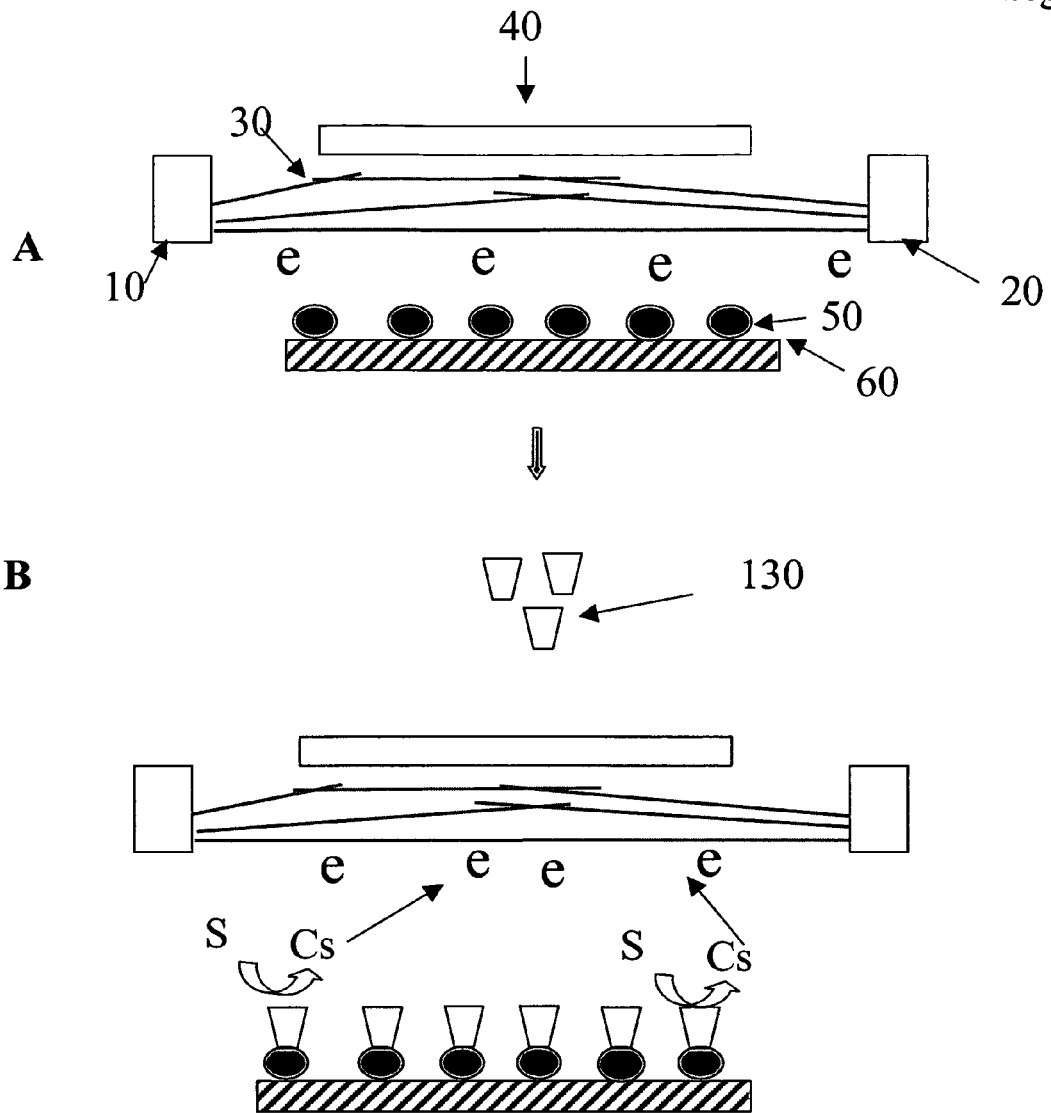

Another embodiment applicable to the detection of a redox catalytic analyte is shown in FIG. 2. Referring to FIG. 2A, the basic elements of the nanosensor are as illustrated in FIG. 1A. The format of the nanosensor is modified to accommodate the addition of a redox catalytic analyte (130), typically an enzyme. Because the analyte has catalytic functionality it may act as a reporter. The redox catalytic analyte (130) binds to the capture moiety (50). A redox active substrate (S) and co-substrate (Cs) that are designed to interact with the bound catalytic analyte are introduced. As in the format described in FIG. 1, introduction of the redox active substrate (S) and a co-substrate (Cs) results in the oxidation of the substrate (S) and the reduction of the co-substrate (Cs) (or vice versa) producing an alteration of the redox potential of the effector solution which is detected as a change in conductance in the CNT.

Figure 3:
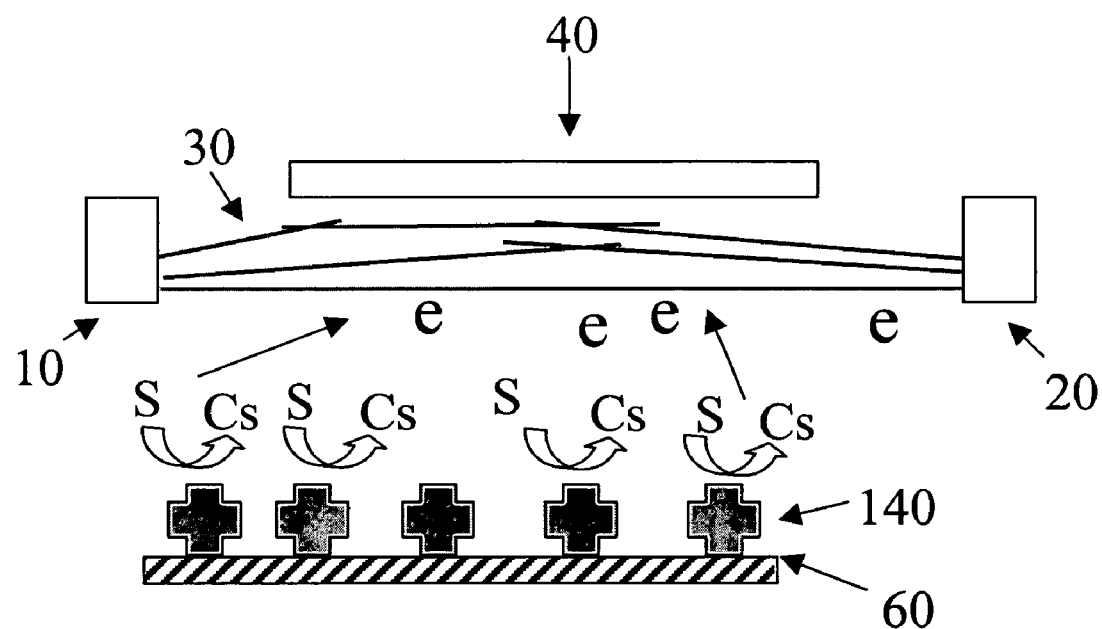
FIG. 3 is a diagram of a nanosensor embodiment with a redox reporter attached to a surface and acting upon a redox active analyte in solution.

Another embodiment applicable to the detection of a redox active analyte is shown in FIG. 3. The basic elements of the nanosensor are as illustrated in FIG. 1A. The format of the nanosensor is modified to accommodate a redox active analyte. Because the analyte is itself a redox active substrate (S), it may be acted upon by a redox reporter. The redox reporter which acts on the redox active analyte (140) is attached to the surface (60). In the presence of a co-substrate (Cs) there is an alteration of the redox potential of the effector solution which is detected as a change in conductance in the CNT.

Figure 4:
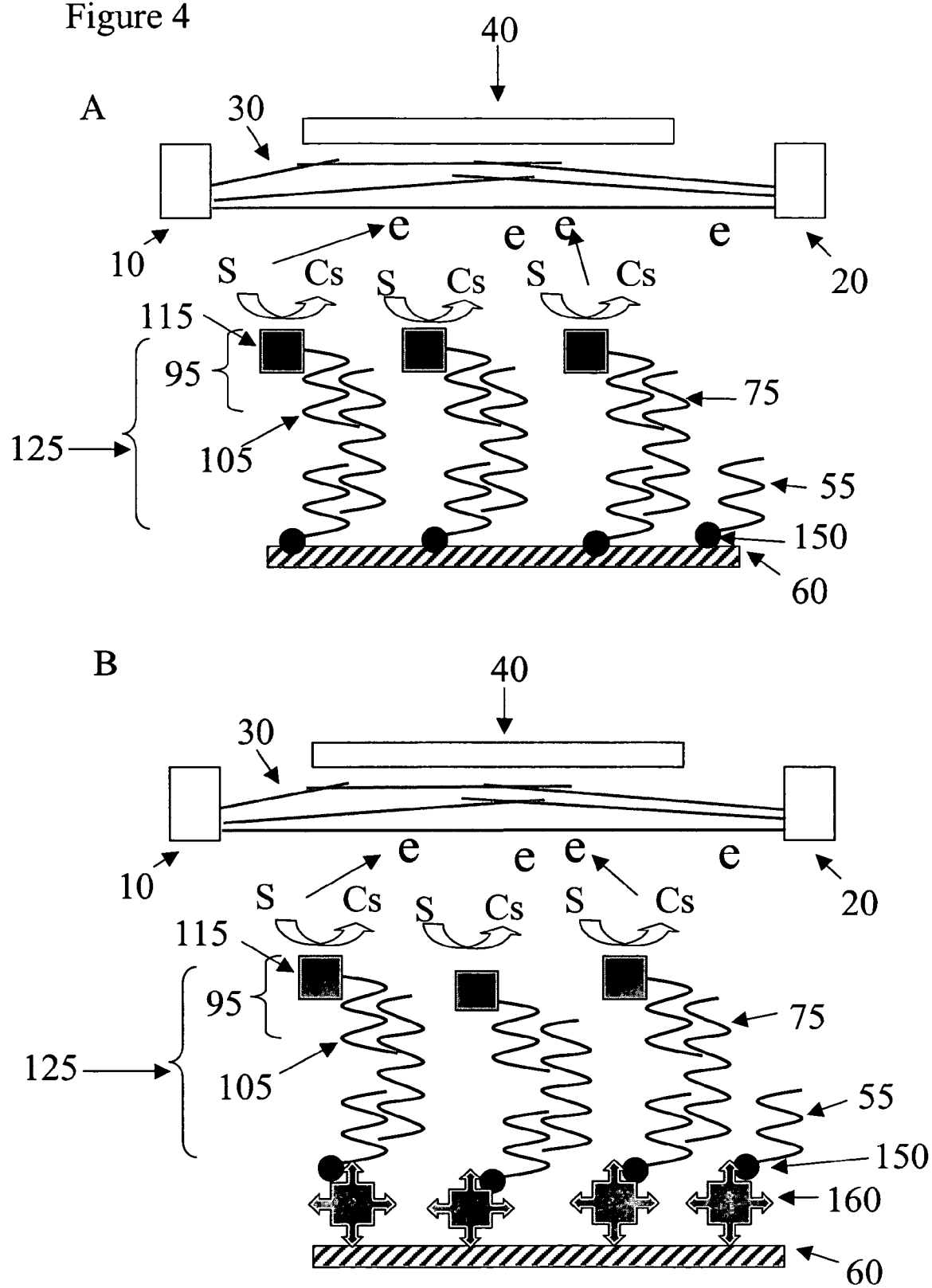
FIG. 4A is a diagram of a nanosensor analogous to FIG. 1 where the analyte is a nucleic acid.
FIG. 4B is a diagram of a nanosensor analogous to FIG. 4A that includes a secondary attachment molecule.

Additional embodiments applicable to the detection of a nucleic acid analyte are shown in FIGS. 4A and 4B. The basic elements of the nanosensor are as illustrated in FIG. 1A. In FIG. 4A the capture moiety (55) is an oligonucleotide that is attached to the surface (60) through an attachment group (150), and has complementarity to a first part of the nucleic acid analyte. The analyte in single-stranded form (75) hybridizes to the capture moiety oligonucleotide (55). The reporter conjugate (95) comprises an analyte receptor (105) that is an oligoucleotide with complementarity to a second part of the nucleic acid analyte, and a reporter element (115). Hybridization occurs between the analyte and the analyte receptor forming a capture-analyte-redox reporter complex (125). Introduction of a redox active substrate (S) and a co-substrate (Cs) results in an alteration of the redox potential of the effector solution which is detected as a change in conductance in the CNT.

In the embodiment in FIG. 4B all elements are the same as in FIG. 4A with the addition of a secondary attachment molecule (160) that serves to attach the capture moiety (55) to the surface (60).

Figure 5:
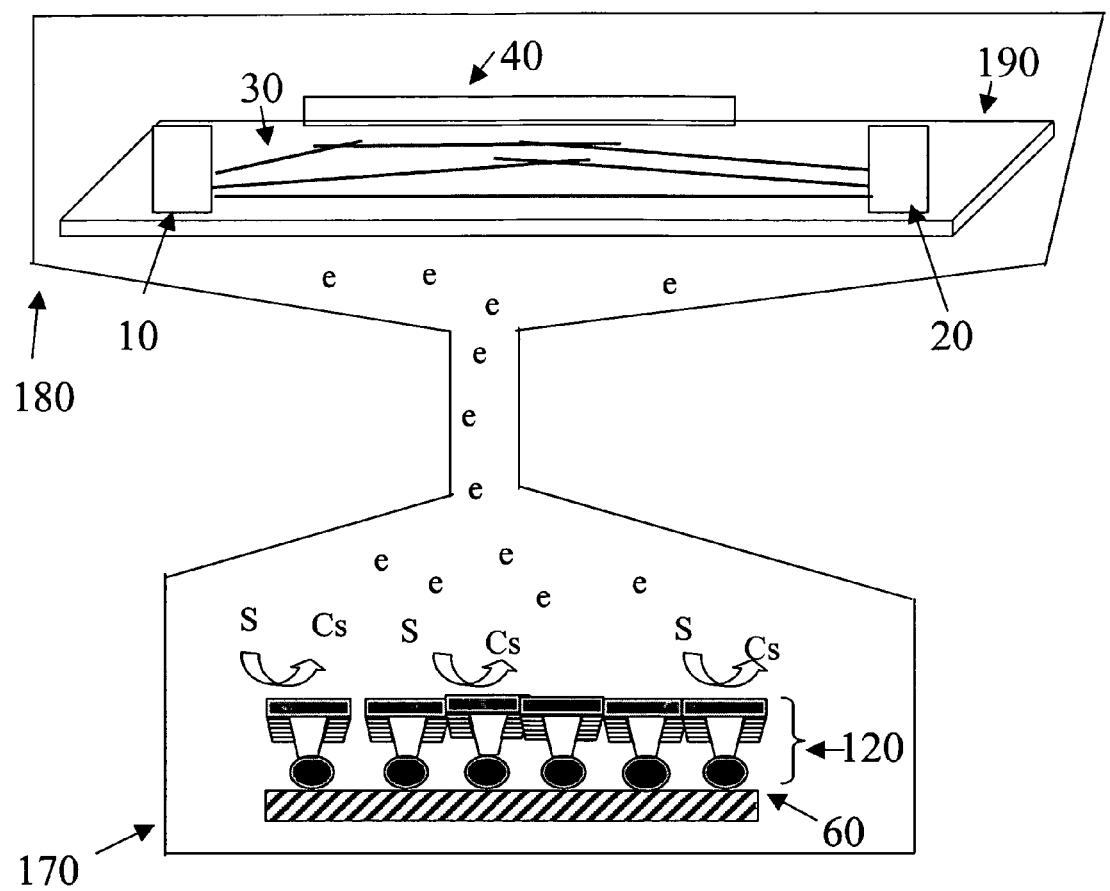
FIG. 5 is a diagram of a nanosensor embodiment with two separate chambers.

Another embodiment wherein the nanosensor includes two chambers and two surfaces is shown in FIG. 5. Elements of the nanosensor described in FIG. 1 are replicated in FIG. 5. In addition, a first surface (60) with attached capture-analyte-redox reporter complex (120) is contained within a first chamber (170) that is connected to a second chamber (180) containing a second surface (190) that supports the CNTs (30), and source and drain electrodes(10, 20). The effector solution flows or diffuses between the two chambers such a change in the effector solution is detected as a change in conductance in the CNT.

Figure 6:
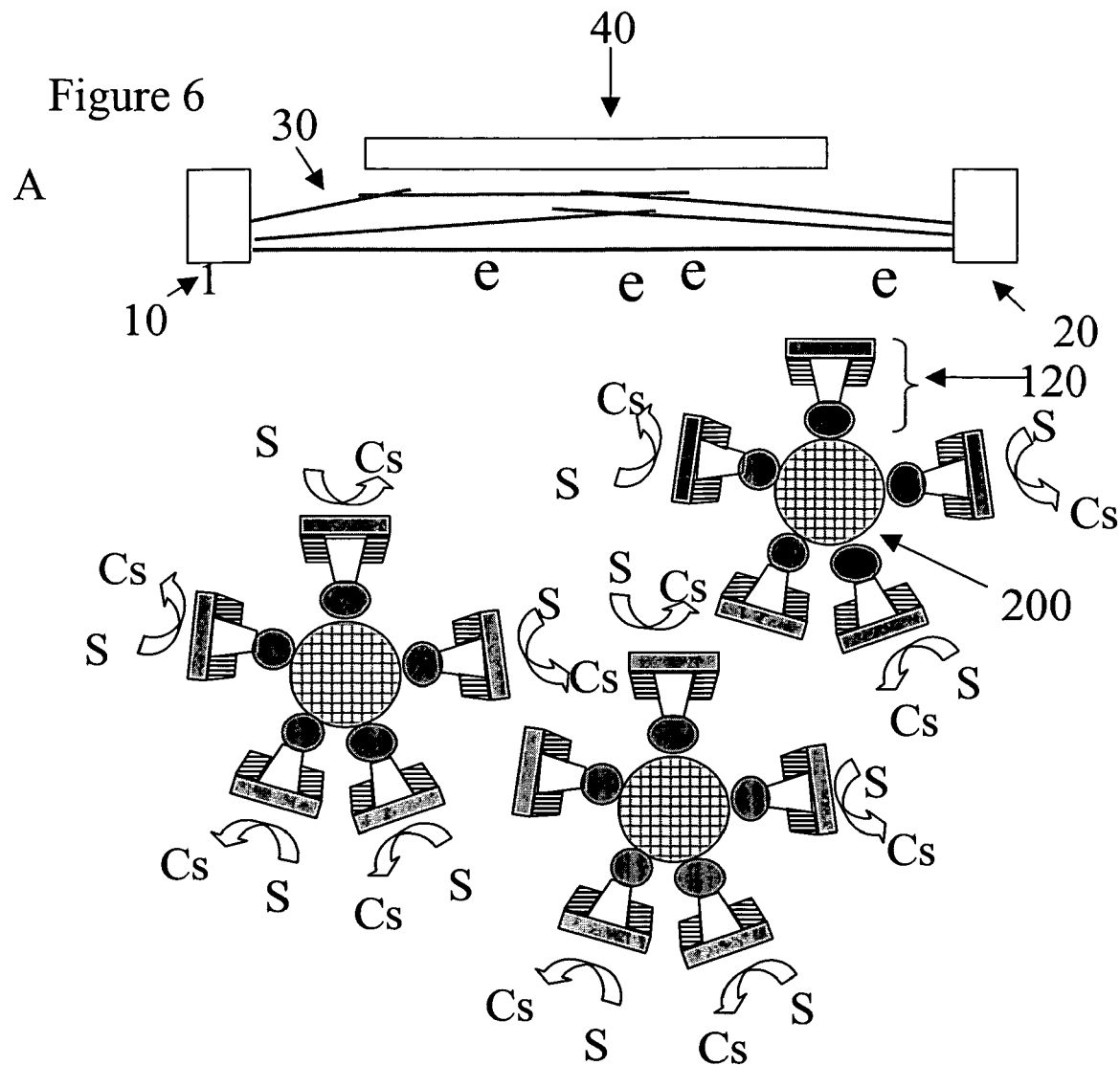
FIG. 6A is a diagram of a nanosensor embodiment where the attachment surface is the surface of beads. 6B is a diagram of an activity switch.

Another embodiment including a surface in the form of beads is shown in FIG. 6A. Elements of the nanosensor described in FIG. 1 are replicated in FIG. 6 with the exception of the surface (60). An alternative type of surface in the form of a bead (200) is the site of attachment of the capture-analyte-redox reporter complex (120).

Figure 6B:
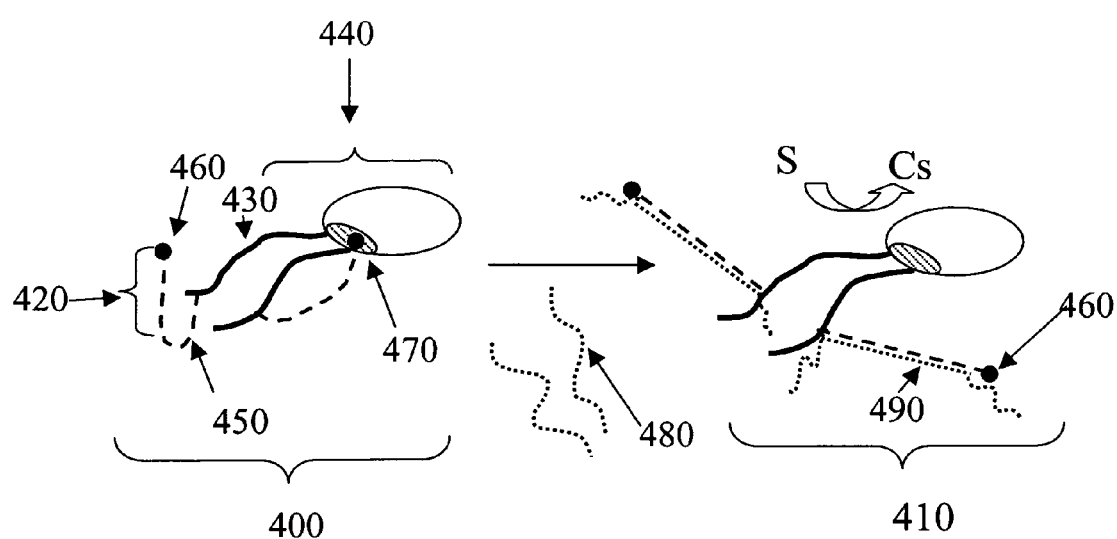
Figure 7:
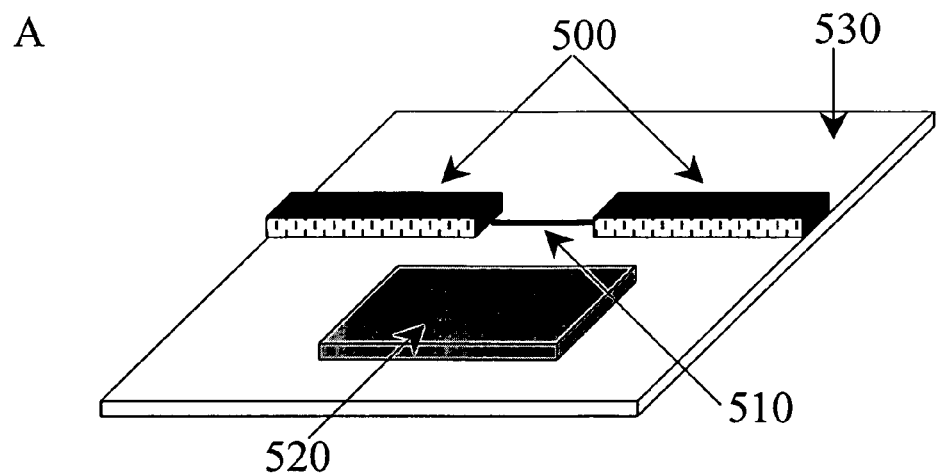
FIG. 7A is a schematic drawing of a nanosensor with an area (pad) for capture moiety attachment that is separate from the CNTs. 7B is a schematic drawing of a polymer stamp forming a micro-fluidic channel, within which lies a surface for capture moiety attachment.
Figure 7:
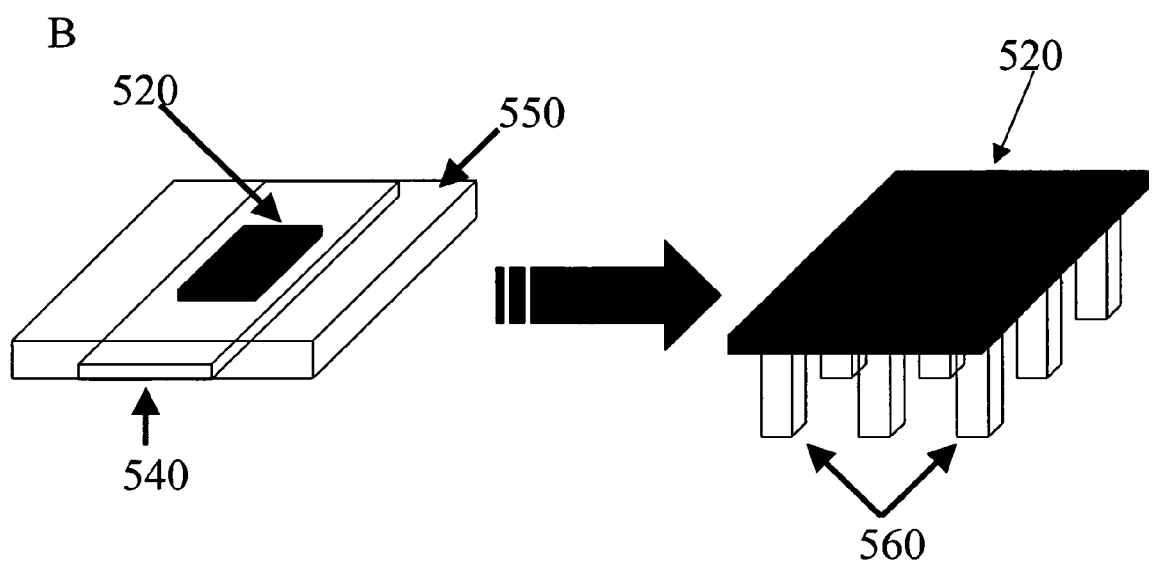

In those instances where the reporter is catalytic, the invention provides a format for the nanosensor where the reporter may be activated and "switched on" by the presence of an analyte. Analytes suitable for detection via an activity switch reporter will be those that have the ability to interact with the reporter and "switch on" the reporter. This format employs what is referred to herein as an "activity switch" and allows greater flexibility in the design of the sensor. A specific embodiment of the activity switch is illustrated in FIG. 6B. In this embodiment the redox reporter is an enzymatic glycoprotein (440), and may exist in either an active (410) or inactive (400) form. One aspect of the glycoprotein (440), is the presence of a point of attachment for an activity switch (420), such as an oligosaccharide chain (430). The activity switch comprises an oligonucleotide (450) anchored via its 5' end to the glycoprotein (440), and an inhibitor (460) attached to the oligo at the 3' end. In this conformation the oligo acts as an analyte receptor for a nucleic acid analyte. In the inactive form (400) the enzymatic glycoprotein (440) has the inhibitor bound to the active site of the protein (470). When the inhibited reporter comes in contact with an nucleic acid analyte (480) that is complementary to a portion of the anchored oligo (450) the resulting hybridization (490) pulls the inhibitor (460) away from the active site of the glycoprotein (440), thus switching on the enzyme, and allowing the oxidation/reduction of the substrate (S) and/or Co-substrate (Cs). One of the key advantages of the present invention is the ability to detect the presence of an analyte on a surface removed from the carbon nanotube. Several formats of the nanosensor will allow for this type of sensing, one of which is illustrated in FIG. 7. Referring to FIG. 7A, the nanosensor is comprised of a silicon chip (530), supporting a pair of electrodes, (500), the electrodes being connected by an electrically conducting path comprising at least one semiconducting CNT (510). The silicon chip may additionally support a "pad" or functionalized surface which is proximal to, but separated from the CNT (520). The pad may comprise a polymer or metallic surface that is itself a capture moiety or acts in conjunction with one, for example, gold for trapping thiolated oligonucleotides or nickel for trapping magnetic beads.

FIG. 7B shows a schematic drawing of a polymer stamp (550) that may incorporate a pad where the stamp has a micro-fluidic channel (540). Within the channel is a surface for capture moiety attachment (520) that has post-like features (560) to increase the surface area.

One of skill in the art will recognize that features of different embodiments as diagrammed in FIGS. 1-7 may be combined, such as the redox catalytic analyte of FIG. 2 being used in a device with separate chambers as in FIG. 5, and the pad (520) shown in FIG. 7A binding the beads of FIG. 6A. For example, in one particularly useful alternate embodiment, the analyte receptor (an oligo for example) and the reporter (such as an enzyme) may be each independently attached to a bead. Specifically a streptavidin coated bead could bind a biotinylated enzyme (reporter) as well as a biotinylated oligo (analyte receptor). The ratio of reporter enzyme to oligo receptor on the bead could be designed so that the reporter enzyme was in excess to the oligo. Thus, upon the binding (hybridization) of an immobilized analtye (a DNA analyte hybridized to a capture moiety oligonucleotide that is attached to a substrate for example) with the receptor oligo linked to the bead, the presence of the anlayte would be detected by a signal, amplified by the increased concentration of reporter enzyme on the bead. In this fashion many reporter molecules could be associated with each analyte. Additionally, in situations where the bead was magnetic, the magnetic properties could be used to concentrate or purify the analyte.

Carbon Nanotubes of the Nanosensor

The nanosensor of the invention comprises at least one semiconducting CNT comprised within an electrically conducting path.

CNTs have diameters on the nanometer scale and a ratio of the length to the diameter, i.e., the aspect ratio, of at least 5. In general, the aspect ratio is between 100 and 100,000. Carbon nanotubes are single-walled hollow cylinders composed primarily of carbon atoms. CNTs of the nanosensors of the invention may be doped with agents such as metals and may have coatings. Preferred CNTs are free of metals.

CNTs may be produced by a variety of methods, known to those skilled in the art, and are additionally commercially available. Methods of CNT synthesis include laser vaporization of graphite (A. Thess et al. *Science* 273, 483 (1996)), arc discharge (C. Journet et al., *Nature* 388, 756 (1997)) and HiPco (high pressure carbon monoxide) process (P. Nikolaev et al. *Chem. Phys. Lett.* 313, 91-97 (1999)). Chemical vapor deposition (CVD) can also be used for producing carbon nanotubes (J. Kong et al. *Chem. Phys. Lett.* 292, 567-574 (1998); J. Kong et al. *Nature* 395, 878-879 (1998); A. Cassell et al. *J. Phys. Chem.* 103, 6484-6492 (1999); H. Dai et al. *J. Phys. Chem.* 103, 11246-11255 (1999)).

Additionally CNTs may be grown via catalytic processes both in solution and on solid substrates (Yan Li, et al., *Chem. Mater.*; 2001; 13(3); 1008-1014); (N. Franklin and H. Dai *Adv. Mater.* 12, 890 (2000); A. Cassell et al. *J. Am. Chem. Soc.* 121, 7975-7976 (1999)).

One or more CNTs may be present in the nanosensor as part of an electrically conducting path. The CNTs may take any conformation however single-walled CNTs are preferred. At least one of the CNTs between the source and drain electrodes must be semiconducting to provide an electrically conducting path that can be controlled by a gating electrode. Multiple CNTs of varying chirality may be joined to provide the electrically conducting path.

The CNTs may be suspended between the source and drain electrodes of the nanosensor, or supported on a surface. A gating electrode in the nanosensor generates an electric field to change the CNT conductance such that the sensitivity of the CNTs to the presence of the effector can be optimized. The gate is an electrode separated from the CNT by a dielectric material and polarized relative to the drain electrode. The gate may be a back gate, a top gate or a split gate for operation in air. An electrode that contacts a solution in the CNT chamber may be used for operation as a liquid gate.

Since the redox potential of the effector in solution provides the signal for detection by the CNT, there is no requirement for close proximity between the CNT and the capture moiety or redox reporter. This feature allows the CNT to be in any location accessible either by diffusion or flow, including such transport processes as pumping and injecting, of the effector solution. For example, the CNT may be on the same surface as the capture moiety or on a surface different from that of the capture moiety as long as the solution containing the redox effector may contact both surfaces at the same time or sequentially.

The surface of the CNT may be functionalized or coated to enhance or increase the specificity of the detection of the redox potential of the solution. Coatings such as PEG, PEI, PFE, polylysine, polyglutamic acid, and polystyrene sulfonic acid may be added to control non-specific binding or the binding of charged species.

The exact structure of the nanosensor is not specified by the nanosensor of the invention. Any sensor structure may be employed with the components of the invention wherein the CNTs come in contact with a solution in which a redox potential is changed.

Analyte and Capture Moiety

The present invention is designed to detect the presence of an analyte. The analyte may be any substance that is amenable to being captured and immobilized near a surface, however biomolecules are particularly suitable. Analytes that are targets may be, for example, chemicals and biomolecules. Preferably, biomolecules are analyte targets of the invention. An analyte may be a nucleic acid that is either DNA, PNA (peptide nucleic acid) or any type of RNA, for example ribosomal RNA, messenger RNA, and antisense RNA. An analyte may be a protein, a polypeptide, or a peptide. An analyte may be a virus, a cell such as a prokaryotic cell including a bacterial cell, or a eukaryotic cell such as a plant or an animal cell. An analyte may be a metabolite of a biological organism or a product produced by a biological organism.

The capture moiety binds the analyte when it is present in the test sample. The capture moiety may be any molecule that can bind to an analyte and the two form a binding pair, with each being a binding partner. The binding pair may be two polypeptides, a polypeptide and a nucleic acid molecule, a polypeptide and a chemical, two chemicals, a nucleic acid molecule and a chemical, or any type of combination where the analyte is one member. If an analyte is a protein, an antibody recognizing an epitope of that protein is a binding partner. If an analyte protein naturally binds to another protein such as two proteins in an enzyme complex, these two proteins are binding partners. Another type of protein/protein binding pair is a protein and its receptor. In any of these cases, either the entire protein or only the binding portion of a protein may be used as a binding partner. If an analyte is a DNA molecule, having a sequence that naturally binds to a protein such as a transcription factor, then the transcription factor protein or a binding portion thereof and the target DNA molecule form a binding pair. Examples of well-known binding pairs include hapten/anti-hapten, glutathione-S-transferase/glutathione, 6x histidine Tag/Ni-NTA, streptavidin/biotin, S-protein/S-peptide, cutinase/phosphonate inhibitor, folic acid/folate binding protein, protein A/protein A immunoglobulin and protein G/protein G immunoglobulin.

In addition, complementary single stranded nucleic acid molecules are binding partners. The capture moiety binding partner has a sequence complementary to at least a portion of the sequence of a target nucleic acid. If a target nucleic acid molecule is double stranded, then the capture moiety may have complementary sequence to either strand of the target. The strand that is captured by the capture moiety will usually also be complementary to the analyte receptor oligonucleotide. Prior to detection the double stranded DNA is melted into two free single strands. Capture of a nucleic acid single strand and the steps that follow are carried out below the melting temperature. One skilled in the art will know the length of the nucleic acid strand required to have stable hybridization and the conditions of the assay required to maintain the double strand during detection. In addition triple strand nucleic acid formations may be used as capture moiety, analyte, and analyte receptor. Methods for hybridization are well known in the art, see for example Sambrook supra.

An optional aspect of the present invention is to distinguish a nucleic acid molecule target that is completely complementary to an oligonucleotide probe capture moiety from one that has one or more mismatches. Assay conditions such as salt concentration and temperature may be adjusted to allow hybrids only of completely matching nucleic acids to be stable. Determination of appropriate hybridization stringency conditions to use with a specific polynucleotide probe and target nucleic acid molecule pairs is well known to one skilled in the art.

Capture Moiety Attachment

In several embodiments the invention relies on the presence of a capture moiety to immobilize the analyte on a surface. Generally the capture moiety is affixed on the surface or support. The capture moiety may take a variety of forms. In some instances the capture moiety will bind the analyte which will additionally be bound to a reporter conjugate as described in FIG. 1. Alternatively the capture moiety will bind the analyte, which will itself serve the reporting function as described in FIG. 2. In some instance the reporter will itself will be immobilized on the surface (as described in FIG. 3).

Irrespective of its form, the capture moiety or redox reporter must be affixed to a surface. That surface may be the surface of the carbon nanotube of the nanosensor but is more typically and preferably the surface of a support. The capture moiety may be on the same support surface as the CNTs or on a separate support surface from the CNTs.

Nanosensor Surfaces and Supports

The nanosensor may include a first and a second support. The first support, when included, provides a surface for placement of the CNTs and source and drain electrodes which form an electrically conducting path. The first surface may be comprised of any non-conductive material. Examples include, but are not limited to, silicon, polysilicon, silicon dioxide, silicon nitride, polymeric materials, glass, agarose, nitrocellulose, nylon, and insulating materials. Particularly useful are silica chips. Typically silica chips have a thin layer of natural oxide, which has very low electrical conductivity and is an insulator. For better insulation of the surface from the underlying silica, a thicker oxide layer that is typically about 500-600 nm may be added, by a method such as with a thermal treatment in air, for example. This provides additional insulation from the underlying silica.

The function of the second surface or support is for the attachment of the capture moiety. The surface to which the capture moiety is attached may be located adjacent to the CNTs, not adjacent but within the same chamber as the CNTs, or in a separate chamber from the CNTs, as long as the solution with altered redox potential can contact the CNTs. In addition, the second support may be the same as, or the same as a portion of, the first support. Some materials which may be used in a second support include silicon, silicon dioxide, silicon nitride, polysilicon, polymeric materials, glass, agarose, nitrocellulose, nylon, ferromagnetic materials, carbon, metals such as gold and nickel and insulating materials as well as semiconducting materials and functional polymers.

Preferably the capture moiety is on a surface that is within about 100 μm from the sensing CNTs. Where the surface is a support, the support may be of any shape, including for example a stamp, a sheet or film, a sphere such as a bead, and a tube. A bead may be for example a magnetic bead, a hydrogel bead, a solid bead, a silica coated bead, or other type of bead. Particularly suitable is a surface area of about $10^4$ μm$^2$, one example of which is diagrammed in FIG. 7A. The capture moiety surface area, as exemplified in FIG. 7A, may be a support such as a pad or a stamp. An example of a pad is an area of gold to which a capture moiety oligonucleotide may be attached using a thiol group. An example of a stamp is deposition of silane in the area for oligonucleotide capture moiety attachment. In designing the stamp it may be useful to pretreat the surface with silicon nitride except in the stamp area to block silane binding, and thus block capture moiety attachment.

Particularly useful is a support surface that is different from that on which the carbon nanotubes are placed. This separate surface can be processed independently of the CNT support surface and placed onto the CNT support surface as a stamp. This nanosensor structure allows the use of different stamps with the same CNT support, thus reducing the setup time and total cost. The stamp may be made using various types of polymers including resins, epoxies, and flexible polymers like polydimethylsiloxane (PDMS), using standard molding processes. Molds may be of any material where features on the mold can be made at a micron scale such as metallic, glass, quartz, silicon and polymer molds. The stamp may have different types of molded surfaces—e.g. flat or channeled. In a particularly useful design, a separate functional polymer stamp has a micro-fluidic channel to which the capture moiety is attached (FIG. 7B). The channel is placed over the CNTs and pressed to the CNT support surface. Fluids containing analytes and detection components of the nanosensor are passed through the channel, making contact with the capture moieties and allowing CNT sensing of changes in redox potential. The surface bearing capture moieties may include post-like features (FIG. 7B) in order to increase the surface available for capture moiety attachment, thus increasing the sensitivity of detection. This type of capture moiety attachment structure may make up a portion of the stamp, with the post-like features extending into the micro-fluidic channel. Alternatively, polymer or silica-based beads with attached capture moieties may be deposited on top of the stamp following capture of the analyte and binding of the redox reporter conjugate.

An attachment group may be added to a capture moiety to use in attaching it to a surface. For example, a capture moiety molecule may be attached to a gold surface using a thiol group. The capture moiety molecule may be linked to a silica surface using a silane containing reactive groups.

Optionally, the capture moiety may be attached to a surface through non-covalent interaction with a secondary attachment molecule. For example, streptavidin may be attached to the surface and the capture moiety may be derivatized with biotin so that it will be attached to the surface through the interaction between biotin and streptavidin. Additional examples of such secondary attachment systems include glutathione-S-transferase/glutathione, 6× histidine Tag/Ni-NTA, S-protein/S-peptide, cutinase/phosphonate inhibitor, antigen/antibody, hapten/anti-hapten, folic acid/folate binding protein, and protein A or G/immunoglobulins. The fabrication of areas for capture moiety attachment can be achieved using methods such as lithography, micro-contact printing and ink-jet printing of molecules tethered to functional groups, which can anchor capture moiety molecules.

Optionally the surface may be coated with a material to facilitate attachment of the capture moiety. For example, the coating may be a polymer such as poly(ethylene imine) that provides amine groups to facilitate binding of proteins or polynucleotides. The surface may be silanated using a silanation reagent. One skilled in the art will be familiar with different silanation reagents that may be used to add different reacting groups such as amines, carboxylic acids, thiols, and aldehyde groups onto surfaces to act as attachment sites. For example aldehyde groups may be added to surfaces for attachment of oligonucleotides containing hydrazide or amine linkers. Examples of chemistries that may be used for attachment with silane reactive groups include hydrazine-aldehyde chemistry and succinimidyl-6-hydrazinonicotinate acetone hydrazone (SANH) chemistry.

Following capture moiety attachment, a surface may be treated in order to reduce non-specific binding of molecules. This treatment or passivation of the surface may include not only the surface for capture moiety attachment, but also the surface of the CNT support (where separate), especially between the electrodes. For example, when nucleic acid analytes and probes are to be used in a nanosensor, reduction of non-specific binding may be achieved by (1): coating the surface with blocking reagents (e.g. polyethylene glycol) or (2) blocking solutions (e.g. casein), both of which prevent non-specific binding of nucleic acids.

Redox Reporter Elements

The redox reporter of the invention is responsive to the presence of an analyte and interacts with a redox active substrate and co-substrate. Within the context of the present invention both the redox active substrate and co-substrate must be present for analyte detection. In a preferred embodiment the redox reporter is an enzyme (e.g. laccase) and the redox active substrate is an enzymatic substrate (e.g. $ABTS^-_2$) and the co-substrate is an additional redox active molecule that serves as an electron drain or source for the substrate (e.g. oxygen). In this specific case, both the substrate and co-substrate bind to the reporter where the substrate is oxidized, making electrons available to the co-substrate. Here the substrate, which is also the effector, becomes oxidized and in turn oxidizes the CNTs.

In one configuration, the redox reporter may be in the form of a redox reporter conjugate, comprising the redox reporter as one element and an analyte receptor as a second element. The analyte receptor functions to specifically bind an analyte.

Enzymes that may be used as redox reporters, and molecules that are their substrate/co-substrate pairs are, for example, laccase and phenols/$O_2$, and $ABTS^{2-}/O_2$, glucose oxidase and glucose/$O_2$, bilirubin oxidase, and bilirubin/$O_2$, cholesterol oxidase and cholesterol/$O_2$, alcohol dehydrogenase and alcohols/$NAD^+$, lactate dehydrogenase and lactate/DCPIP (dichlorophenol indophenol), D-amino acid oxidase and D-alanine/$O_2$.

The presence of a redox effector is another aspect of the redox reporting system described herein. The redox effector is in contact with the CNT and has the ability to "effect" a change in the redox potential of the redox solution and to participate in rapid electron transfer with CNTs. In one embodiment, the redox effector may be either the redox reporter substrate or the co-substrate. In an alternate embodiment, the effector may be another molecule. Thus the redox effector may be any molecule that has its redox potential in the solution changed as a consequence of the presence of an analyte substrate and where that change in redox potential is mirrored in the CNTs. The redox potential is either shifted to more positive or more negative potential. Enzymes may be used as a redox reporter or catalyst and the analyte may itself be the redox effector. For example, the enzyme laccase is a redox reporter that oxidizes the substrate $ABTS^{2-}$ at the expense of $O_2$. The redox couple $ABTS^{-1}/ABTS^{-2}$ is the redox effector. Other examples are lactate dehydrogenase where the oxidation of lactate is coupled to the reduction of DCPIP, glucose oxidase where the oxidation of glucose is coupled to the reduction of $O_2$ to $H_2O_2$ which can in turn oxidize other mediators such as ABTS, and alcohol dehydrogenase, where the oxidation of alcohols can be coupled to the reduction of $NAD^+$ to NADH.

The redox reporter of the reporter conjugate is linked to an analyte receptor that binds to the analyte. The analyte receptor and analyte together form a binding pair, with each being a binding partner, as defined above.

Linking of a redox reporter to an analyte receptor is accomplished such that the activity of the redox reporter is maintained. Processes for protein-protein or protein-nucleic acid linking are well known to one skilled in the art. (G. T. Hermanson (1996) Bioconjugate Techniques, Academic Press, New York)

The use of a redox reporter conjugate greatly increases the sensitivity of analyte detection due to the amplification of the signal by the catalytic turnover of the redox reporter. Many more redox active effector molecules are oxidized or reduced in the catalytic reaction mediated by the redox reporter than the number of analyte molecules captured from the test sample. This amplification process allows the assay of microliter size samples containing limited analyte molecules and makes the system amenable to small scale screening applications.

If the analyte is itself an enzyme that catalyzes a reaction involving a redox active substrate and co-substrate, then no additional redox catalyst is required in the nanosensor (as in FIG. 2).

Redox Reporter with Activity Switch

In one embodiment, the redox reporter molecule is modified to include an activity switch that can regulate the enzymatic activity of the reporter molecule. In this embodiment, the redox reporter with the activity switch is attached to a surface, and no separate capture moiety is included.

In the present invention the activity switch has two components: an inhibitor that binds to the active site or an allosteric site of the reporter molecule (enzyme) thereby blocking its activity, and an analyte receptor that binds to the target analyte. An inhibitor is particularly useful when the dissociation constant of the inhibitor for its binding site on the enzyme is substantially lower than that of the substrate for its binding site, which may or may not be at the same site. This difference in dissociation constant provides that the inhibitor is able to prevent the substrate from binding.

The activity switch may be attached to the reporter molecule directly, or if the reporter molecule has oligosaccharide chains, the activity switch may be attached to these chains. For example, the enzymatic glycoproteins glucose oxidase and laccase have oligosaccharide chains which are locations for activity switch attachment.

In the present embodiment the analyte receptor may be any molecule which can bind to the target analyte and which allows the inhibitor to access the active site or allosteric site in the free state but does not allow access upon binding to the target analyte. The analyte receptor may be, for example, a protein, a polypeptide, an oligopeptide, a peptide nucleic acid, an oligonucleotide, a polynucleotide or any nucleic acid. Preferred is a single stranded oligonucleotide probe, attached via the 5' end to the reporter molecule and linked at the 3' end to an inhibitor of the enzyme activity. It is understood that the attachments at the 5' and 3' ends can be switched without impact on the function. The oligonucleotide, which is highly flexible in its single stranded form, is able to bend such that the inhibitor binds to the active site or allosteric site, blocking the action of the enzyme on its reporter substrate. Upon hybridization of the complementary strand of the analyte DNA (or RNA) to the enzyme-bound oligonucleotide probe, the double stranded DNA (or DNA/RNA hybrid) is now much more rigid than the single strand, with a persistence length some 60-fold greater than that of the single stranded probe oligonucleotide. The inhibitor can then no longer bind to the active site or allosteric site of the enzyme, which is turned on.

The active enzyme is now able to promote electron transfer between the redox active substrate and co-substrate, thereby modifying the redox potential of the redox effector. One skilled in the art will know the length of analyte receptor required to have stable hybridization and the conditions of the assay required to maintain the double strand during detection. It is particularly useful for hybridization of the oligonucleotide analyte receptor to the analyte nucleic acid to drive the dissociation of the inhibitor from its binding site. This occurs when the decrease in free energy associated with hybridization of the analyte receptor to the analyte exceeds that associated with the binding of the inhibitor to the enzyme.

One key utility of the activity switch is that its use eliminates the need for separation of components of the nanosensor. Where the activity switch is being employed, the assay may take place in the presence of the enzyme substrate and washing the nanosensor to remove excess enzyme would not be necessary. This is the case because the enzyme reporter is only active and able to receive substrate when the analtye has been bound by the analyte receptor.

A preferred embodiment of the activity switch is an oligonucleotide analyte receptor attached at one end to a laccase inhibitor and at the other end to a laccase enzyme. Preferred laccase inhibitors are tetrachloro-o-quinol, tetrafluoro-o-quinol, 3,4-dihydroxy-2,6-dichloro-benzaldehyde, and substituted hydrazone of 3,4-dihydroxy-2,6-dichloro-benzaldehyde. Any methods for attaching compounds to DNA, and DNA to proteins may be used. Preferred attachment of the inhibitor to DNA is through a maleimide group on maleimide-dPEG$_4$-NS ester coupled to 3,4-dihydroxy-2,6-dichlorobenzaldehyde through hydrazine derivatization. Preferred attachment of DNA to laccase is by aldehyde-hydrazide attachment chemistry.

Redox Effector and Redox Mediator

As has been discussed above, the redox reporter of the invention reacts with a redox active substrate and co-substrate to change the redox potential of an effector solution comprising an effector molecule. In one embodiment the effector molecule may be either the substrate or co-substrate. Optionally the effector molecule may be another molecule.

Redox species that can interact rapidly and reversibly with CNTs to alter their conductance may be a redox effector. The redox effector is a molecule whose redox potential is changed under the influence of the redox reporter. The redox effector may be either one of the two redox reporter substrates (redox active substrate and co-substrate), or may be another molecule. Generally, one of the substrates acts as an electron donor or acceptor and the co-substrate undergoes reduction or oxidation, respectively. The redox potential of one of the substrates may then be sensed by the CNTs because it is able to donate or accept electrons rapidly and reversibly to or from the nanotubes. This species is the redox effector. The other substrate may react slowly or not at all with the CNTs. This species is less visible to the CNTS. The log of the ratio of the concentration of the oxidized to the concentration of the reduced form of the redox effector determines its solution redox potential.

Both substrates must be present for analyte detection. One may already be present and not require separate addition such as when oxygen acts as one of the substrates.

Optionally, it may be necessary to introduce an electron mediator into the system to facilitate electron transport to the effector solution. For example, if neither substrate from the redox reporter reaction is effective in substantially changing the CNT conductance, a redox mediator may be necessary. An example of a redox mediator is DCPIP (dichlorophenol indophenol) which may be reduced by the bound flavin of lactate dehydrogenase (redox reporter) in which lactate (substrate) is oxidized and the bound flavin (co-substrate) is reduced. DCPIP(ox)/DCPIP(red) can then act rapidly and reversibly with the CNTs to change their redox potential. Molecules that may function as mediators include, but are not limited to, o-quinones, p-quinones, dichlorophenol indophenol (DCPIP), 2,2'-azino-bis(3-ethylbenz-thiazoline-6-sulfonate (ABTS$^{-2}$), nicotinamide adenine dinucleotide (NAD$^+$/NADH), phenazine, phenoxazine and phenothiazine derivatives, and Os-complexes.

Removing Unbound Target Analyte and Unbound Reporter Conjugate

Unbound molecules are removed at specified stages during the analyte detection processes shown in FIGS. 1 and 2. Unbound analyte that does not bind to surface attached capture moiety molecules is removed. Likewise, any redox reporter conjugate that is not associated with bound analyte is removed. Removing these unbound molecules may be achieved by washing with an appropriate buffer, as would be known to one skilled in the art.

Redox Potential

The present invention relies on the presence of an analyte to alter the redox potential of an effector solution in contact with a CNT. The changes in the effector redox potential alter the conductance of the CNT, thereby producing a change in current (the signal).

Applicants have found that single-walled semiconducting carbon nanotubes show redox behavior as a general property, such that the concentration of charge carriers of the CNT is reversibly sensitive to redox molecules capable of oxidizing and/or reducing the CNT. Depending on the redox potential (proportional to the log of the ratio of the oxidized to the reduced state), an electron transfer reaction can take place between the redox molecules and the carbon nanotube, hence changing the density of charge carriers of the nanotube, which in turn causes a shift in the source-drain current vs. gate voltage plot. For example, the oxidation of the nanotube by a suitable oxidant results in an increase in the hole concentration in the valence band, which shifts the Isd vs gate voltage toward positive gate voltages. Likewise, the reduction of the nanotube by a suitable reductant decreases the concentration of holes in the valence band and therefore shifts the plot toward negative gate voltages. This phenomenon is applicable to the monitoring of any redox process, preferably to sense the presence of biomolecules using the nanosensors and methods of the present invention.

Samples

Samples that may be assayed for the presence of an analyte using nanosensors and methods of the present invention include biological samples as well as non-biological samples. For example, a sample may be from a cell, tissue or fluid from a biological source including a human, an animal, a plant, fungus, bacteria, virus, etc. The source of a sample is not limited and may be from an environmental source, from food or feed, produced in a laboratory, or other source.

Method for Analyte Detection

In methods for analyte detection shown in FIGS. 1 and 2, components of the nanosensor are added in stages or steps. The sample is added such that it is in contact with the capture moiety, allowing the analyte to bind to the capture moiety. After binding goes to completion, analytes that did not bind to the surface-attached capture moiety molecules are removed. Removing these unbound molecules may be achieved by washing with an appropriate buffer, as would be known to one skilled in the art. If a redox reporter conjugate is included in the embodiment followed, a solution of the redox reporter conjugate is then added such that it is in contact with the capture moiety-analyte complex. Following binding, any redox reporter conjugates that are not associated with the capture moiety-bound analyte are removed, again by washing. The analyte solution may also be placed in contact with the redox reporter conjugate first and in contact with the capture moiety either secondarily or simultaneously, after which unbound species are removed by washing. The redox-active substrate and optionally the co-substrate are added such that they are in contact with the redox reporter or a redox catalytic analyte and the redox potential of the effector in solution is changed as a result.

In the method for analyte detection shown in FIG. 3, the sample is added such that it is in contact with the redox reporter and the redox potential of the solution is changed as a result of interaction between the redox reporter and the redox active analyte.

In all three methods for analyte detection, the solution with the altered redox potential may already be in contact with the CNTs if the CNTs and the capture moiety and redox reporter are in the same chamber. If the CNTs, on the one hand, and the capture moiety and redox reporter on the other are separated, then the solution with altered redox potential is brought in contact with the CNTs by diffusion or pumping. The solution with altered redox potential may flow through a channel, tubing, or other conduit to come in contact with the CNT. The conductance of the CNTs is then measured and compared to a measure of the CNT conductance that was taken prior to adding the sample or at the earliest time following the addition of the sample. Measurement of the CNT conductance is made by applying a dc (direct current) bias voltage between the source and drain electrodes while varying the gate voltage. In addition, the signal to noise ratio may be improved by ac (alternating current) modulation of the bias voltage. Alternatively, the CNT conductance is measured by holding the gate voltage constant and recording the current as a function of time. A gate electrode is preferred but not required.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "h" means hour(s), "min" means minute(s), "µL" means microliter(s), "mL" means milliliter(s), "nm" means nanometer(s), "mm" means millimeter(s), "cm" means centimeter(s), "µm" means micrometer(s), "mM" means millimolar, "µM" means micromolar, "M" means molar, "V" means volts, "mV" means millivolts, "Vg" means gate voltage, "Vsd" means source-drain voltage, "Isd" means source-drain current, "p-type" means charge carrier type (e.g. hole), "CVD" means chemical vapor deposition. HiPco stands for high pressure carbon monoxide.

Example 1

Oxidation and Reduction of a Single-Walled Carbon Nanotube Device

Nanotube devices, prepared as follows, were purchased from Molecular Nanosystems (Palo Alto, Calif.). Single-walled carbon nanotubes were grown from catalyst pads in a CVD furnace at 900° C. The catalyst pads were patterned on a thermally oxidized surface (500 nm thick) of a (100) silicon wafer. After the growth, less than or equal to 5 nm of Ti, 50 nm of Pd and less than 50 nm of Au layers were deposited sequentially onto the $SiO_2/Si$ surface to form electrical contacts with the nanotubes.

The metallic nanotubes present in the gap (2 micron) were destroyed, by ramping the bias voltage from 0 to 10V while holding the back gate voltage at 0V. This procedure, performed in air, enhanced the ON-OFF ratio of the devices to ~3-4 orders of magnitude. The electronic properties of the remaining semiconducting nanotubes were monitored by applying a fixed bias voltage between the source and drain electrodes while changing the back gate voltage.

Figure 8:
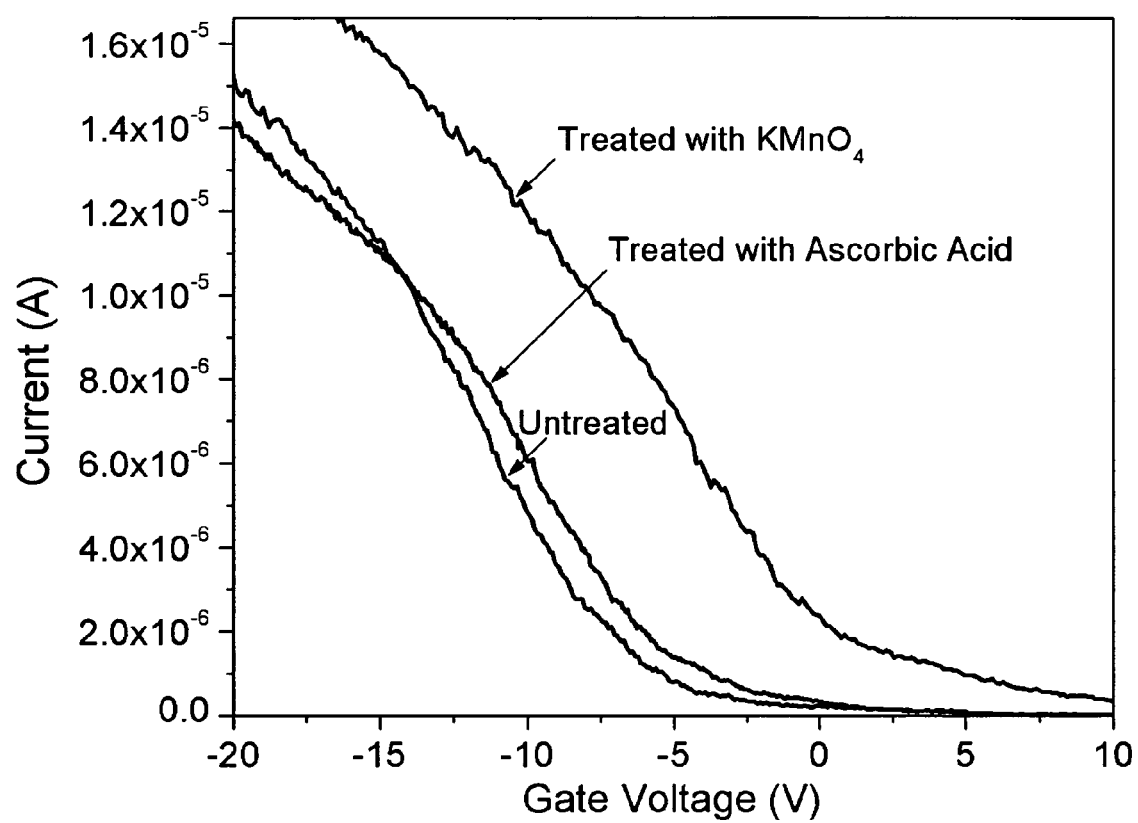
FIG. 8 shows the current vs gate voltage characteristics of single-walled carbon nanotubes treated with $KMnO_4$ and ascorbic acid. The measurements were performed in air using a back gate.

The source-drain current vs gate voltage characteristics of a semiconducting single-walled carbon nanotube device, recorded using a back gate in air were determined for untreated and redox molecule treated devices (FIG. 8). The curve labeled "Untreated" shows the Isd vs. Vg characteristics of the device with no further treatment. A drop (~20 µL) of 100 µM of $KMnO_4$ was placed on top of the carbon nanotube device for ~15 min and then rinsed with ultrapure deionized water (EASYpure II, Barnstead Inc. Dubuque, Iowa). After drying with a gentle stream of $N_2$, the Isd vs. Vg curve was again recorded. As shown by the curve labeled "Treated with $KMnO_4$", this treatment produced a significant shift of the current vs gate voltage characteristics to positive gate voltages. This shift is due to the oxidation of the carbon nanotube by permanganate ions, which increases the concentration of free p-type carriers. The carbon nanotubes of the device were re-reduced by treatment with a similar sized drop of 100 mM of ascorbic acid placed on top of the device and similarly incubated, rinsed and dried. As shown by the curve labeled "Treated with Ascorbic acid", this treatment produced a shift of the Isd vs. Vg characteristics back to the original position. This shift is due to the decrease in the concentration of the p-type charge carriers through reduction by ascorbic acid. This example illustrates that redox molecules were able to modulate the electronic properties of single-walled carbon nanotube devices.

Example 2

Sensitivity of the Conductance of a Single-Walled Carbon Nanotube Device to Solution Redox Potential A flow cell of 4.4 µl volume was mounted and sealed around a carbon nanotube device using an O-ring. The flow cell allowed the device to come in contact with different solutions.

Figure 9:
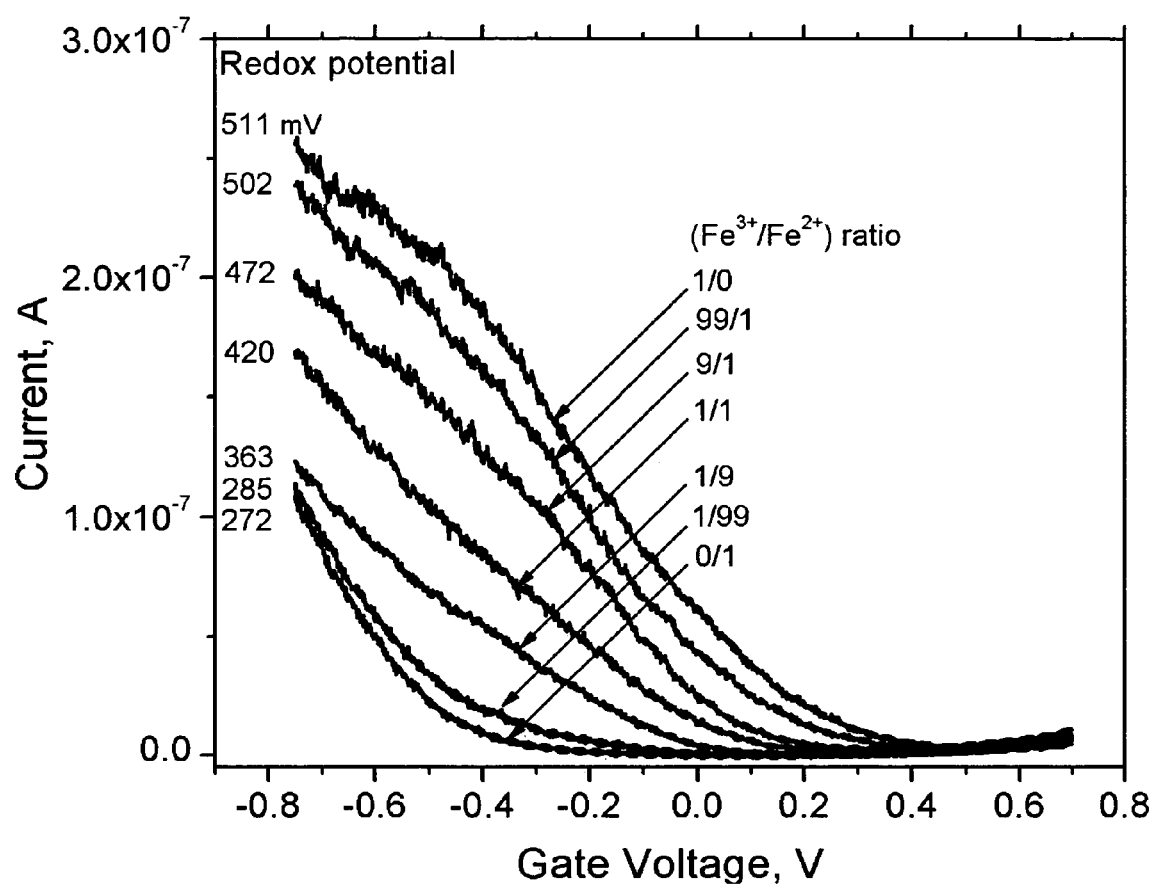
FIG. 9 shows the current vs gate voltage characteristics of a single-walled carbon nanotube device recorded at various redox potentials.

The source-drain current vs gate voltage characteristics were recorded on a single-walled semiconducting carbon nanotube device covered in 50 mM glycine buffer, pH 9.0. An electrode adjacent to the device and in contact with the same solution was used as a liquid gate and scanned from +0.7 to −0.75 V. The source-drain voltage was fixed at 50 mV. A family of buffer solutions was prepared containing various ratios of $K_3Fe(CN)_6$ to $K_4Fe(CN)_6$, the concentrations of which totaled 1 mM. The redox potential of each solution was measured using a Pt and Ag/AgCl combination redox electrode (Orion model 967800). Listed in FIG. 9 are the redox potentials of each solution expressed versus the standard hydrogen electrode (SHE). Each solution was separately placed in the flow cell in contact with the carbon nanotube device and the current vs gate voltage characteristics were recorded in each case using liquid gate scanning. The Isd vs. Vg curves were increasingly turned on at higher gate potentials as the solution redox potential was increased (FIG. 9). This behavior reflects the oxidation and reduction of the carbon nanotubes of the device, with ferri- ($K_3Fe(CN)_6$) and ferrocyamide ($K_4Fe(CN)_6$), respectively, such that as the redox potential increases the concentration of free p-type carriers increases. This behavior was fully reversible, which indicated the ability of the carbon nanotubes to interact with both redox species. Thus this device can be used as a reversible redox sensor of the solution redox potential. This behavior in aqueous solution is in contrast to the data shown in FIG. 8 where the carbon nanotube device was probed in air.

Example 3

Streptavidin and Biotinylated Laccase Coatings on a Chip Containing Single-Walled Carbon Nanotube Devices Silicon chips were prepared for patterned CVD growth of single-walled carbon nanotubes and metal electrode deposition (Molecular Nanosystems, Palo Alto, Calif.). A thermal oxide layer of 500 nm thickness covered the heavily doped silicon, which acted as a backgate. The nanotube devices were incubated overnight at room temperature and then for 24 h at 40° C. in a solution of 1 mg/ml of streptavidin (Molecular Probes) in PBS in a sealed and humidified Petri dish. The chip was washed with water and then incubated for 40 min with biotinylated laccase. The latter was prepared by treatment of 0.48 mg/ml *Trametes versicolor* laccase (Wacker Chemie, Munich, Germany) with 120 mM $NaIO_4$ in 50 mM $NaHCO_3$, pH 7.4 for 60 min at room temperature. The laccase was then washed using a Centricon 30 (Millipore) with 50 mM $Na_2CO_3$, pH 9 to remove the remaining $NaIO_4$ and reacted with 250 µM biotin-cadaverine and 5 mM $NaBH_3CN$ for 2 h at room temperature. The biotinylated laccase was then washed with 50 mM MES pH 5.5 to remove the unreacted small molecules.

Figure 10:
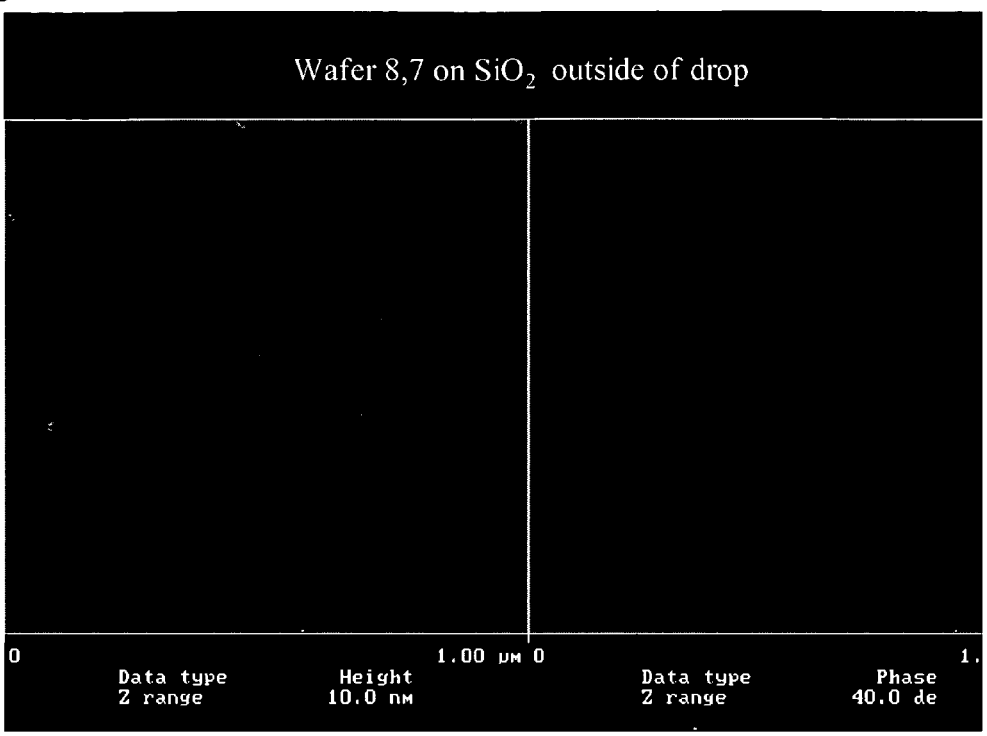
FIG. 10 shows an AFM image of a $Si/SiO_2$ chip (A) outside of region containing surface-bound streptavidin coated with biotinylated laccase and (B) inside region containing surface-bound streptavidin coated with biotinylated laccase.
Figure 10:
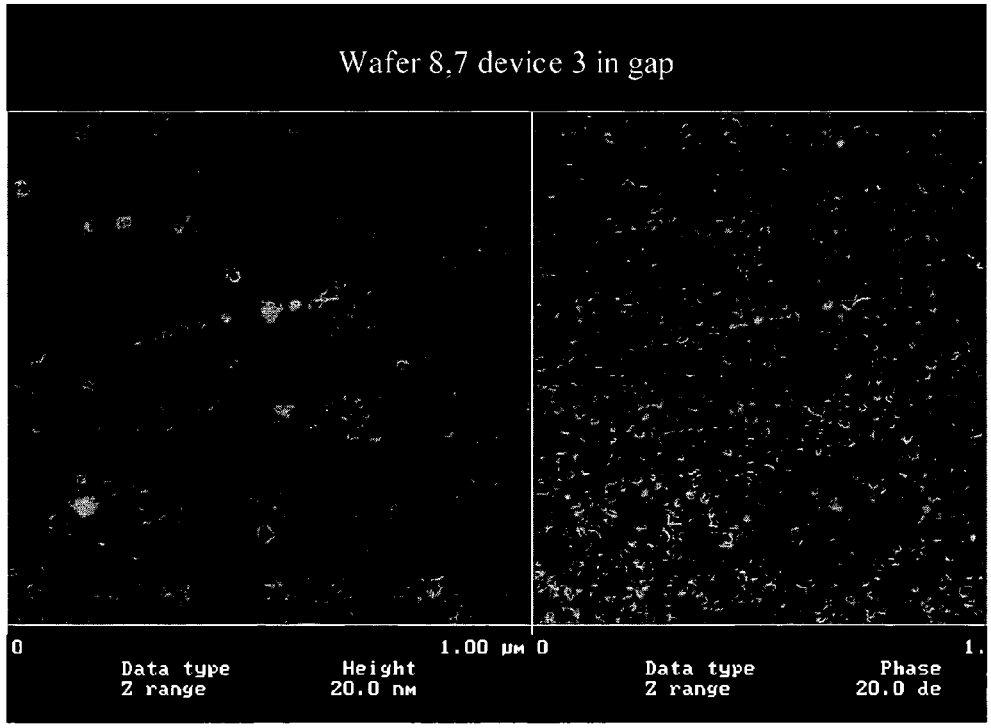

The biotinylated laccase was then bound to the streptavidin layer by incubation for 40 minutes at a concentration of 2.1 mg/mL in 50 mM MES pH 5.5. The unbound laccase was then removed by rinsing with ultrapure deonized water. This treatment produces a monolayer coating of laccase tightly bound to the chip due to the biotin-streptavidin interaction (Kd=$10^{-15}$ M). After the 40 min incubation with laccase, the chip was rinsed with ultrapure deionized water and placed into the flow cell for the electrical characterization described in Example 4. After completing the electrical characterization, the chip was stored in a humidified Petri dish and then examined by atomic force microscopy. Images of the biotinylated laccase monolayer bound to streptavidin are shown in FIG. 10. FIG. 10A shows the region outside the drop where the strepatavidin was deposited onto the chip. The silica surface is quite smooth and free of debris. FIG. 10B shows the region where the streptavidin and biotinylated laccase were placed. The surface is coated with a regular carpet of protein, which, from its thickness, is likely to be a monolayer of streptavidin and laccase.

Example 4

Figure 11:
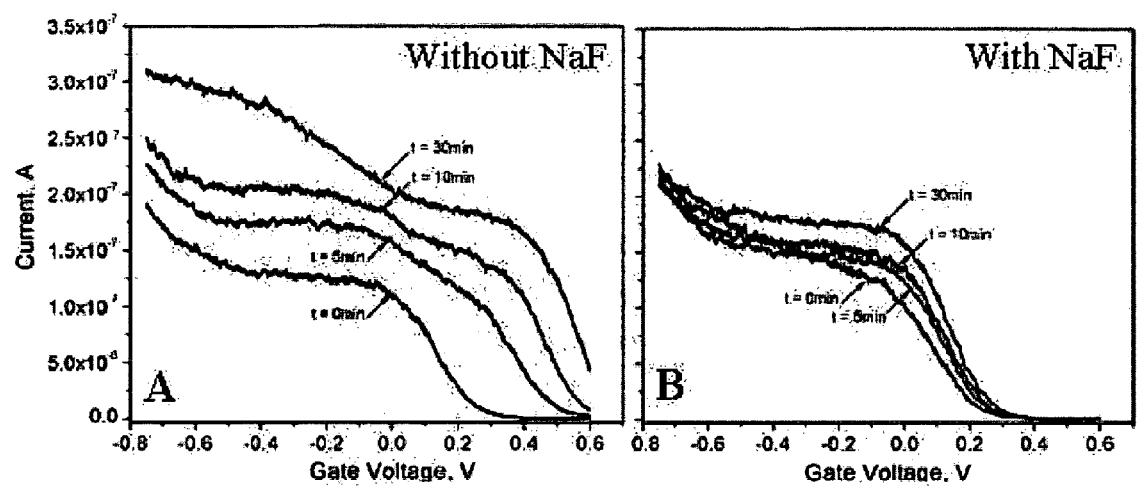
FIG. 11 shows the current vs gate voltage characteristics of a single-walled carbon nanotube device coated with streptavidin and bound to biotinylated laccase: (A) exposed to a 30 μM $ABTS^{-2}$ solution in 50 mM Glycine pH 3.0; (B) exposed to a 30 μM $ABTS^{-2}$ solution in 50 mM Glycine pH 3.0 with 1 mM NaF.

Redox Enzyme-Mediated Oxidation of a Redox Mediator Sensed Via the Conductance of a Single-Walled Carbon Nanotube Device The flow cell was mounted on the single-walled carbon nanotube device that was coated with streptavidin and bound with biotinylated laccase, prepared in Example 3, and the source-drain current vs gate voltage characteristics of the laccase coated device were measured by liquid gating using an electrode adjacent to the single-walled carbon nanotube device. The source-drain voltage was fixed at 50 mV. The device in 50 mM Glycine pH 3.0 exhibited an Isd vs. Vg curve similar to that in the same buffer in the absence of laccase. Upon injection of a 30 µM solution of the redox mediator and laccase substrate $ABTS^{-2}$ (2,2'-azino-bis(3-ethylbenz-thiazoline-6-sulfonate) diammonium salt, Em=650-680 mV) in 50 mM Glycine pH 3.0, the Isd vs. Vg curve first shifted toward negative gate voltages (FIG. 11A, curve t=0 min). This behavior is due to the reduction of the carbon nanotubes by $ABTS^{2-}$. Upon incubation, there is a continuous shift of the Isd vs. Vg curves to positive gate voltages, in the direction opposite to that of the first shift. This positive shift is a consequence of the redox activity of the laccase which oxidizes $ABTS^{2-}$ to $ABTS^{-1}$, at the same time reducing $O_2$ to $2H_2O$. The activity of the redox enzyme results in an increase of the concentration of $ABTS^{-1}$ in the solution, thereby increasing the solution redox potential. The increasing redox potential, in turn, oxidizes the carbon nanotubes, increasing the concentration of p-type charge carriers and causing the Isd vs. Vg curve to shift to positive gate voltages. To prove that these changes are indeed a consequence of laccase activity, 1 mM NaF was added to inhibit the redox activity of the laccase enzyme. As described in Example 5 and shown in FIG. 12, this concentration of NaF inhibits the laccase activity by 95%. FIG. 11B shows the evolution of the Isd vs. Vg curve for the same carbon nanotube device, monitored as a function of time under the same conditions as for FIG. 11A except for the presence of 1 mM NaF. The plots presented in FIG. 11B show a much reduced shift with time of the Isd vs. Vg curve to positive gate voltages. This experiment clearly demonstrates that single-walled carbon nanotube devices can be used for redox-coupled sensing of biomolecules. The presence of an analyte can cause a redox enzyme to be bound to the device, after which the presence of the enzyme can be detected by its redox activity on a suitable redox-active substrate. Alternatively, the redox enzyme can be prebound to the surface of the device such that it can detect the presence of a redox-active analyte by oxidation or reduction of the analyte. In both cases, the enzyme activity produces a change in the solution redox potential, detected by the device.

Example 5

Inhibition of Laccase Activity by NaF

Figure 12:
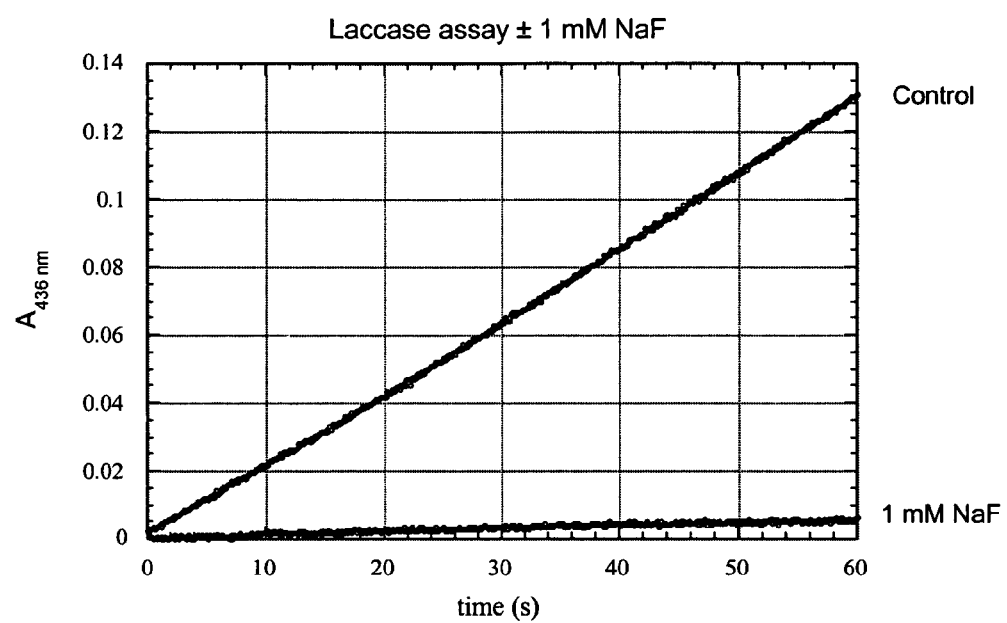
FIG. 12 shows the oxidation of $ABTS^{-2}$ by laccase in 50 mM Glycine pH 3, followed at 436 nm in the presence and absence of 1 mM NaF.

A stock solution of *Trametes versicolor* laccase (4.8 mg/ml) was diluted 200,000-fold into 50 mM Glycine, pH 3.0. At time zero, $ABTS^{-2}$ (2,2'-azino-bis(3-ethylbenzthiazoline-6-sulfonate) diammonium salt was added at a concentration of 5 mM and the oxidation of $ABTS^{-2}$ was followed by monitoring the absorbance change at 436 nm. Shown in FIG. 12 is the result of the laccase assay in the presence and absence of 1 mM NaF. The latter inhibits the laccase activity by 95%.

Example 6

Redox Sensing at a Distance from the Carbon Nanotube Device

Figure 13:
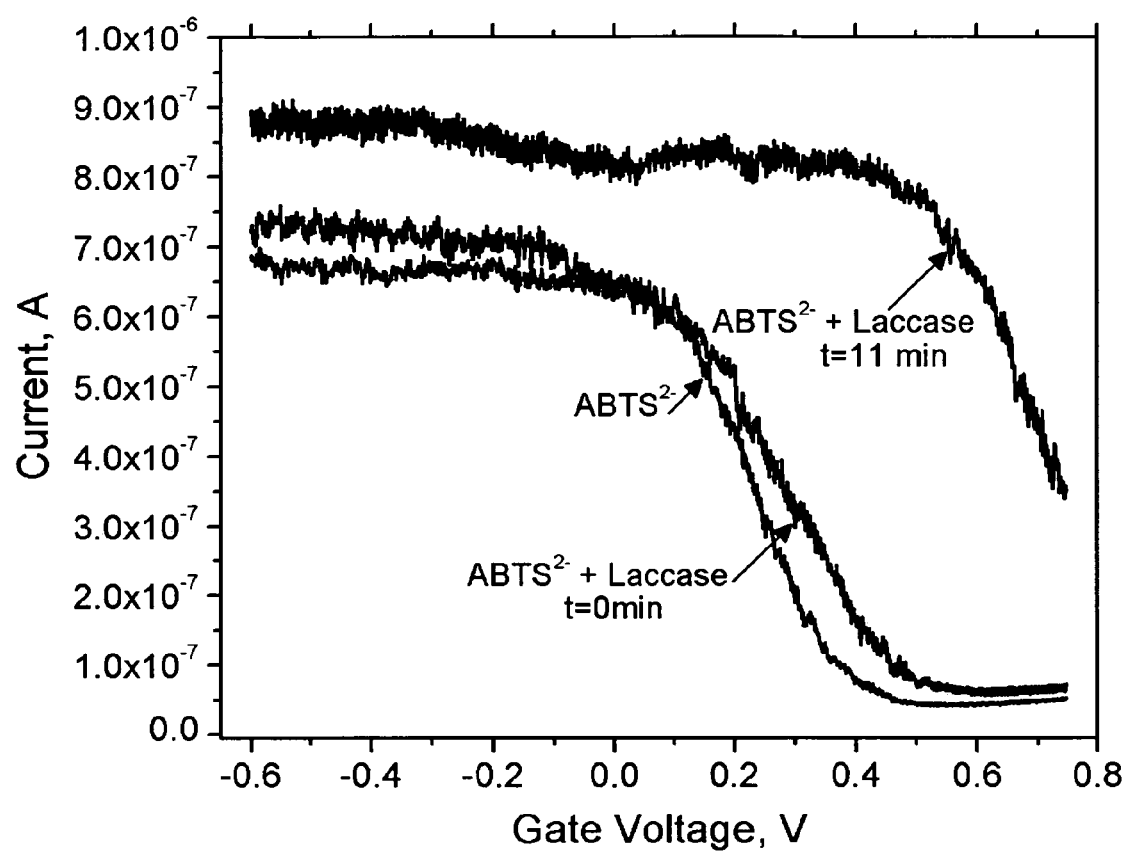
FIG. 13 shows source-drain current vs gate voltage curves of a carbon nanotube device in $ABTS^{2-}$ alone and as a function of time as the $ABTS^{2-}$ is oxidized by the laccase in solution.

The Isd vs. Vg curve of a semiconducting single-walled carbon nanotube device in the presence of 5 mM $ABTS^{-2}$ in 50 mM Glycine pH=3 was measured as a baseline and is shown in FIG. 13. An adjacent electrode served as a liquid gate. Then two solutions, one containing 10 mM $ABTS^{-2}$ in 50 mM Glycine, pH 3 and the other containing 10 µg/mL laccase in 50 mM Glycine, pH 3 were mixed just external to and pumped into the liquid chamber of the flow cell in contact with the device. The flow was stopped and the evolution of the Isd vs. Vg curve followed as a function of time. As time elapsed, a shift of the turn-on of the current toward positive gate voltages was observed. This shift is analogous to that observed in FIG. 11 where the biotinylated laccase was attached to the $SiO_2$ surface of the chip via the biotin-streptavidin link. The results of this experiment show that the presence of laccase molecules on the surface of the carbon nanotube is not required for laccase-mediated redox sensing. Instead, the enzyme molecules can be placed in any convenient location in the device, provided it is within 100 µm of the nanotubes to allow for diffusion of the redox mediator to the nanotubes on the seconds time scale (distance calculated from the expected diffusion coefficient of ABTS).

Example 7

Comparison of the Changes in Electronic and Optical Properties of Single-Walled Carbon Nanotubes During Oxidation A test was developed to show that the modulation of the electronic properties of the nanotubes comes from the oxidation and reduction of the nanotubes themselves. This was done by comparing the change in conductance as a function of time for carbon nanotubes in contact with redox mediators in solution to optical changes occurring in suspended nanotubes under the same conditions. We have previously shown that the oxidation and reduction of single-walled carbon nanotubes can be followed by their Vis/NIR absorbance spectra, where the E11 transitions disappear as the nanotubes are oxidized (M. Zheng and B. A. Diner (2004) JACS 126, 15490-15494). HiPco single-walled nanotubes (Carbon Nanotechnologies Incorporated CNI, Houston Tex.) were surfactant-dispersed and suspended in 50 mM Glycine pH 9.0. The nanotubes under these conditions are partially oxidized, due to the $O_2/2H_2O$ redox couple, which interacts very slowly with the nanotubes. The suspension was then exposed to 1 mM $K_3Fe(CN)_6$ which resulted in a bleaching of the E11 absorbance band (FIG. 14A). A time course for the bleaching was observed at 1138 nm for ten minutes following the addition of 1 mM $K_3Fe(CN)_6$. The addition of 1 mM $K_4Fe(CN)_6$ to a fresh sample produced an evolution in the opposite direction, consistent with a reduction of the partially oxidized nanotubes. The time course of the optical changes was also measured following the addition of a lower concentration of ferricyanide (0.1 mM) such that the time course could be followed more completely, consistent with addition of oxidant and mixing by hand (FIG. 14B). The half time of the bleaching was about 2 min. FIG. 15 shows that upon addition of 0.1 mM $K_3Fe(CN)_6$ to a single-walled carbon nanotube based device there was also a slow evolution of the conductance (Isd) with time to higher values with a half time also of about 2 min. This experiment was done under the same conditions as the spectroscopic experiment of FIG. 14, with a Vsd of 50 mV. This comparison shows that the change in the conductance of the carbon nanotube device in the presence of ferricyanide is due to the oxidation of the nanotubes.

Example 8

Attachment of Oligonucleotides to Silica Chip Surfaces Using Hydrazide-Aldehyde Chemistry Silica chips were coated by vapor deposition with triethoxy-silyl-butyraldehyde by incubation in an evacuated chamber for 6 h in the presence of a pool of liquid silane. The chips were rinsed with acetone and isopropanol, and dried under a stream of $N_2$. The chips were then dried either by heating in a vacuum oven for 1 h at 100° C. or left overnight under dry $N_2$. They were then stored in a glove box under $N_2$ until use.

An oligonucleotide, oligo 28 (SEQ ID NO:1), was designed from the human gene encoding low-density lipoprotein receptor (LDLR, oligo beginning with codon 194), and oligo 29 (SEQ ID NO:2) was designed as the oligo 28 complement. Oligonucleotides 28 and 29, each with a 5'-linked hydrazide, were purchased from Integrated DNA Technologies, Inc. (Coralville, Iowa). These 5'-hydrazide-linked single-stranded oligonucleotide probes (10 μM) in 0.5 M $NaHPO_4$, pH 7.4 were incubated for 1 h on a silane-treated chip, after which the DNA solution was made 25 mM in $NaBH_3CN$ and incubation continued for another 45 min. Incubation was carried out in Petri plates maintained at 100% relative humidity. The chips were then rinsed with deionized water and dried under a stream of $N_2$. Oligonucleotide densities of $10^{12}$ molecules/$cm^2$ were readily attained, as determined by carrying out the same attachment chemistry using oligonucleotide 27, with the same nucleotide sequence as oligo 28, but having in addition a Cyanine 3 fluorescent tag (Cy3) at the 3' end. The fluorescence signal was quantified using a digital camera and compared to a calibration curve using known densities of fluorescent tagged oligonucleotides deposited on the chip surface.

Example 9

Attachment of Oligonucleotides to Silica Chip Surfaces Using Succinimidvl-6-hydrazinonicotinate acetone hydrazone (SANH) Chemistry An alternative route to surface-attached oligonucleotides involves making the SANH derivative of a 3'-amino terminated oligonucleotide. SANH was purchased from Solulink (San Diego, Calif.). Attachment through the 3' end is required for single-stranded analyte DNA to be detected through bridging an oligonucleotide probe bound to laccase and the oligonucleotide probe bound to the chip surface as diagrammed in FIG. 16. In this diagram, 101 is the silica chip, 102 is the oligonucleotide probe with its 3' end attached to the silica chip surface, 103 is single stranded analyte DNA, 104 is an oligonucleotide probe attached to laccase, which is 107. The polarity of the oligonucleotides and single stranded analyte DNA are shown using 5' and 3' designations.

SANH-Derivatized Oligonucleotide

Oligonucleotides 51 and 53 (SEQ ID NO:3), each with the same sequence and a 3'-amine, but oligo 53 additionally having a 5' Cy3 tag, were purchased from Integrated DNA Technologies, Inc. (Coralville, Iowa). To 10 μL of 3'-amine-terminated oligonucleotide in $H_2O$ (1 mM) were added 2 μL of 0.5 M $NaHPO_4$, pH 7.4. Then DMF (0.6 μL) was added as was 4.33 μL SANH in DMF (solution: 1 mg SANH in 100 μL DMF). The total of 17 μL was incubated for 3 h at room temperature. After incubation, the reaction mix was diluted to 500 μL with $H_2O$ and spun in a Biomax 5 spin filter. The sample was washed two more times with water to remove unreacted SANH and stored at −80° C.

Attachment to Surface

Silane-treated chips were prepared as described in Example 8 above. The chips were then incubated for 2 h, at room temperature with 10 μM SANH-derivatized oligonucleotide 51 or 53, each dissolved in 100 mM Na Acetate pH 5.0. Incubation was carried out in Petri plates maintained at 100% relative humidity. Following incubation, the chips were rinsed with $H_2O$ and dried under a stream of $N_2$.

The fluorescence signal arising from oligo 53, attached to the chip surface, was quantified using a digital camera and compared to a calibration curve using known densities of fluorescent tagged oligonucleotides deposited on a chip surface. The surface density of oligo 53 was on the order of $10^{13}$ molecules per $cm^2$.

To increase the specificity of hybridization, the chips were incubated with Sigma #6429 1× Blocking buffer for 1 h. Excess blocking solution was removed by rinsing with 50 mM Na Acetate pH 5.0 plus 100 mM $Na_2SO_4$. Surface-bound oligonucleotide 51 was hybridized separately to:

1) Oligonucleotide 52 (SEQ ID NO:4), acting as a target sequence, hybridized to oligonucleotide 54 (SEQ ID NO:5). Oligonucleotide 54 has 18 nucleotides complementary to the 3' end of the target oligonucleotide 52 and a fluorescent tag, Alexa Fluor 546, at its 5' end. Oligonucleotide 52 has at its 5' end 18 nucleotides complementary to oligonucleotide 51.
2) Oligonucleotide 52 (SEQ ID NO:4), acting as a target sequence, hybridized to oligonucleotide 50 (SEQ ID NO:5). Oligonucleotide 50 has the same nucleotide sequence as oligonucleotide 54 and was attached to laccase enzyme (lac/oligo 50) as described below in Example 13, This oligonucleotide also has a Cy3 tag at its 3' end.

All oligonucleotides were purchased from Integrated DNA Technologies, Inc. (Coralville, Iowa). Oligos 52 and 54 in (1), and oligos 52 and 50 in (2) were prehybridized in 50 mM Na Acetate pH 5.0 plus 100 mM $Na_2SO_4$ for 10 min at 50° C., then allowed to cool to room temperature before adding to the chip with oligo 51.

Hybridizations of the surface bound probe, oligo 51, with the samples listed above were carried out in 50 mM Na Acetate pH 5.0 plus 100 mM $Na_2SO_4$. Unbound oligonucleotides were removed by rinsing with Washing Buffer A (Arraylt, Telechem International Inc., Sunnyvale, Calif.). Where a laccase/DNA adduct was used for hybridization, 50 mM Na Acetate pH 5.0 plus 100 mM $Na_2SO_4$ was used for the wash. After washing, the chip was covered with a cover slip and observed using a fluorescence microscope. The extent of hybridization was evaluated by measuring fluorescence emission from fluorescent-tagged oligonucleotides attached or not to laccase.

Results of fluorescent signals following hybridizations in 1) and 2) above, using different concentrations of oligos as listed, are given in Table 1. Controls of non-complementary oligo hybridizations and incubation under hybridization conditions with periodate-treated laccase labeled directly with Alexa Fluor 555 hydrazide were close to background levels. The fluorescence signals for both hybridizations 1) and 2) were dependent upon added oligo concentration, indicating that the target oligo did hybridize to the surface-attached oligo 51, and that both the Alexa Fluor-labeled oligo 54 and the laccase-coupled oligo 50 were hybridized to the free end of the hybridized target oligo 52. Thus the capture moiety (oligo 51) did capture the target analyte (oligo 52) and an analyte receptor (oligo 50) in the redox reporter conjugate (lac/oligo50) did bind to the target analyte.

TABLE 1

Fluorescence signals following hybridization to surface bound oligo.

| Concentration | Camera exposure | Relative signal amplitude |
|---|---|---|
| 1 nM Oligo52 + Oligo54 | 30 s | 39, 50 |
| 10 nM Oligo52 + Oligo54 | 30 s | 940, 990 |
| 100 nM Oligo52 + Oligo54 | 30 s | 1140, 1690 |
| 1 nM Oligo52 + Lac/Oligo50 | 30 s | 100 |
| 10 nM Oligo52 + Lac/Oligo50 | 30 s | 180 |
| 100 nM Oligo52 + Lac/Oligo50 | 30 s | 200, 350 |

Hybridizations were also performed as in (1) except that analyte oligo 52 was added to the surface attached oligo 51 first, followed by hybridization to fluorexcent-tagged oligo 54. Similar results to those shown above were obtained.

Example 10

Attachment of DNA to Surfaces of CNT Device

The silica surfaces of two chips containing, on their surfaces, carbon nanotube devices were coated first with tri-ethoxy-silylbutyraldehyde by vapor phase deposition in vacuo for 5.5 h. The chips were then either heated in a vacuum oven for 1 h at 100° C. or left overnight under dry $N_2$. Two perfectly complementary oligonucleotides, oligo 28 and oligo 29 (SEQ ID NOs:1 and 2, respectively), each bearing a 5' hydrazide group (1-link, Integrated DNA Technologies, Inc., Coralville, Iowa), were dissolved separately at 50 μM in 100 mM sodium acetate, pH 5.5. Ten μL of oligo 28 solution were placed in the region of one chip where the CNT devices were located and 10 μL of oligo 29 solution were placed in the region of a second chip where the CNT devices were located, and both were allowed to incubate for 45 min at room temperature under conditions of 100% relative humidity. The devices were rinsed with deionized water, dried under a stream of $N_2$, and treated for 15 min with 25 mM $NaBH_3CN$ plus 60 mM ethanolamine in 50 mM $NaHPO_4$, pH7.4. The chips were again rinsed with dionized water, dried under a stream of $N_2$ and stored overnight in a sealed Petri dish containing a moistened towel at 4° C.

Example 11

Detection of DNA Hybridization by CNT Device

Detection of DNA hybridization in a CNT device was assayed as diagramed in FIG. 17. This diagram shows a simplified strategy for demonstrating the ability to detect analyte DNA by detecting hybridization of oligonucleotide-decorated laccase to a surface-bound oligonucleotide probe. In the diagram, two electrodes are indicated, one source electrode (10) and one drain electrode (20), where the electrodes are connected by an electrically conducting path comprising at least one semiconducting carbon nanotube (30). A third electrode (40) generates an electric field to gate the conductance of the CNT. Nucleic acid molecules, functioning as capture moieties (220) are attached to a surface (60) through a silyl butyraldehyde attachment group (230). An oligonucleotide (260) that hybridizes to the capture moiety nucleic acid is attached to the enzyme laccase (270). Laccase oxidizes $ABTS^{-2}$ (2,2' azino-di-(3-ethylbenzthiazoline-sulfonate) at the expense of $O_2$, transferring 4 electrons from $4ABTS^{-2}$ to $O_2$, producing $4ABTS^{-1}$ and $H_2O$. Thus the redox potential of the redox effector ($ABTS^{-2}/ABTS^{-1}$) in solution becomes more positive. This change in effector redox potential oxidizes the CNTs, increasing their p-type conductance.

The chips with oligonucleotides 28 or 29 (SEQ ID NOs:1 and 2) attached to the silica surface, prepared in Example 10, were incubated for 30 min at room temperature with oligo 28/laccase adduct at a concentration of 50 nM (in DNA) in a 4.4 μL flow cell. The oligo 28/laccase adduct was prepared as described in Example 13. After incubation, both chips were again rinsed and soaked with 50 mM glycine buffer (pH=3) in the flow cell for 5 min to remove unbound oligo28/laccase.

Electron transport through the CNT was first recorded in the 50 mM glycine pH=3 buffer and immediately after flowing 30 μM $ABTS^{-2}$ in the same buffer into the flow cell. As can be seen from FIG. 18, the oligo28/laccase adduct paired with the oligo 29-coated chip (FIG. 18A) produced more rapid changes in the current vs. gate voltage (Vg) as compared to the same adduct paired with the oligo28-coated chip (FIG. 18B). A look at the changes of the current as a function of time at Vg=−0.4V (FIG. 19) indicated a 3.5 fold more rapid increase in current with the complimentary oligonucleotides as compared to the non-complementary set. This experiment showed that the oligonucleotide/laccase adduct was recognized and preferentially bound by the surface attached complimentary oligonucleotides.

This experiment demonstrated the ability to use complementary oligonucleotides to anchor laccase to a surface and to detect the presence of the enzyme via the enzymatic oxidation of $ABTS^{-2}$. The same principles demonstrated by this example can be applied in a sensor device where the oligonucleotide probe on the laccase and that on the surface are both complementary to and bridged by the analyte single-stranded DNA/RNA to be detected. The rate at which the nanotube current increases is proportional to the amount of laccase bound which is in turn proportional to the amount of analyte single-stranded DNA bound.

Example 12

Discovery of Organic Inhibitors of Laccase and Testing with Linker

High potential quinones/quinols were screened to identify those with characteristics that would be suitable for use as an inhibitor of laccase, to be used in an activity switch. Potential inhibitors were chosen from a set of molecules with reduction potentials high enough so as not to be oxidized by laccase in the presence of $O_2$; a reduction potential greater than that of the copper centers of *Trametes versicolor* laccase, (0.78-0.79

V vs. NHE). Potential inhibitors were tested for the following characteristics:

1) A dissociation constant <50 µM, well below the dissociation constant, Kd of 120-240 µM of the laccase substrate $ABTS^{-2}$.
2) Retention of inhibitor activity when tethered to a linker that would be tethered to DNA.

Compounds were evaluated by varying the concentrations of inhibitor and substrate ($ABTS^{-2}$) and measuring under each condition the rate of $ABTS^{-2}$ oxidation. Plots of the reciprocal of the rate versus the inhibitor concentration at various substrate concentrations gave, at the intersection point, -Ki, the negative of the dissociation constant of the inhibitor. Tetrachloro-o-quinol and tetrafluoro-o-quinol, shown in Diagram I, had Kds, of 7-9 µM and 2.5 µM, respectively, as determined from the data in FIG. 20.

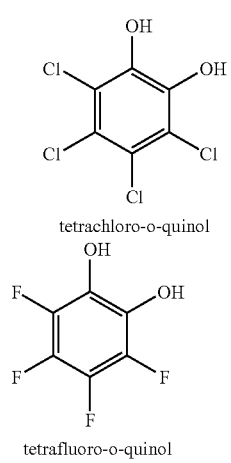

Diagram I tetrachloro-o-quinol tetrafluoro-o-quinol

Since tetrachloro-o-quinol was an effective inhibitor, tetrachloro-p-quinol was also tested. The latter was inactive as an inhibitor, indicating the likely importance of having the hydroxyl groups ortho to each other. This arrangement strongly suggested a role for these groups in the coordination of the Type I copper center of the enzyme. This conclusion was strengthened by the observation that the binding of tetrachloro-o-quinol to laccase caused a decrease in the amplitude of the laccase 600 nm absorbance peak, dominated by a charge-transfer band involving the Type I copper center and its cysteinyl ligand.

Preparation of 3,4-dihydroxy-2,6-dichloro-benzaldehyde as Starting Point for Construction of Inhibitor for Switch The compound 3,4-dihydroxy-2,6-dichloro-benzaldehyde (Diagram II) has a structure which we have determined to be effective in laccase inhibition (described above) as well as a functional group for preparation of the activity switch.

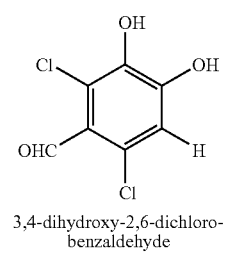

Diagram II 3,4-dihydroxy-2,6-dichloro-benzaldehyde

A test of the ability to attach a linker to the inhibitor and retain inhibitory activity involved synthesis of 3,4-di-OH-2,6-di-Cl-benzaldehyde followed by coupling it to Biotin-dPEG$_4$-hydrazide (Diagram III), thereby adding a tail of ~2.5 nm to the inhibitor.

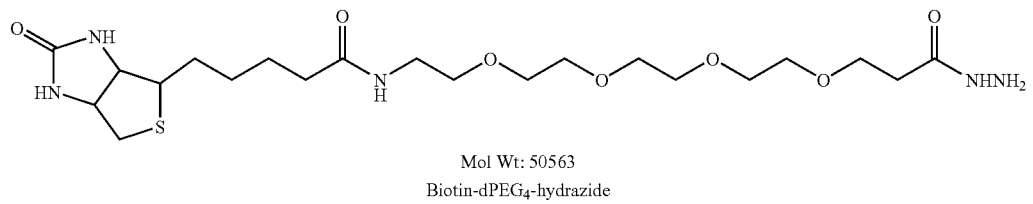

Diagram III

Mol Wt: 50563
Biotin-dPEG$_4$-hydrazide

Into an oven-dried, three-neck round bottom flask, fitted with a thermometer, 1.0 g (4.52 mmol; Aldrich, Milwaukee, Wis.) of 2,6-dichloro-3-hydroxy-4-methoxybenzaldehyde and 45 mL of dichloromethane were added under nitrogen atmosphere. The solution was cooled to −65° C. and 1.32 mL (14 mmol) of boron tribromide was added dropwise. The reaction mixture was left to warm up slowly to room temperature with stirring for 16 hours. The reaction mixture was carefully quenched with the addition of 5 mL of water, then transferred to a single-neck round bottom flask and volatiles were removed in vacuo. The residue was taken up with 50 mL of ethylacetate and washed three times with water and two times with brine. The organic layer was dried over MgSO$_4$, then concentrated to yield 0.9 g (96%) of crude 2,6-dichloro-3,4-dihydroxybenzaldehyde, as an off-white solid, which was used without further purification. H-NMR δ (d$_6$-acetone): 6.85 (1H, s), 9.1 (2H, br s), 10.2 (1H, s). Melting point=213-215° C.

Attachment of 2,6-dichloro-3,4-dihydroxybenzaldehyde to Biotin-dPEG$_4$™-hydrazide Biotin-dPEG$_4$™-hydrazide (15 mg, 30 nmol, Quanta BioDesign, Ltd.; Powell, Ohio) and 2,6-dichloro-3,4-dihydroxybenzaldehyde (6.2 mg, 30 nmol) were dissolved in CH$_2$Cl$_2$ (1.5 mL) and stirred at ambient temperature for 18 hours. After the addition of sodium cyanoborohydride (6 mg, 100 nmol), the reaction mixture was stirred for an additional 2 hours, washed with water (2×0.5 mL) and dried on a rotavap. The 3,4-di-OH-2,6-d i-Cl-benzaldehyde coupled Biotin-dPEG$_4$-hydrazide was evaluated by varying the concentrations of inhibitor and substrate (ABTS$^{-2}$) and measuring under each condition the rate of ABTS$^{-2}$ oxidation. Kinetic plots of 1/V versus inhibitor concentration, [I], showed a Kd of 4.5 to 7.5 μM. Thus the addition of a ~2.5 nm tail to the inhibitor did not impair the ability of the molecule to inhibit laccase activity.

Example 13

Preparation of Activity Switch

Attachment of DNA to Laccase

A single-stranded oligonucleotide probe was attached to laccase using aldehyde-hydrazide attachment chemistry. Laccase from *Trametes versicolor* (6.2 μM; Wacker Chemie GmbH, Munich, Germany) was treated with NaIO$_4$ (120 mM) in 100 mM Na Acetate pH 5 for 1 h at room temperature. Ethylene glycol (120 mM) was then added to quench the unreacted periodate. The oxidized laccase was washed twice by diluting in 100 mM Na Acetate pH 5.0 and concentrating in an Amicon Ultra-4 (30,000 MWCO) (Millipore; Billerica, Mass.). A third wash was carried out in 0.5 M NaPO$_4$, pH 7.4. Overall wash was 1600-fold.

Periodate-treated laccase (32.5 μM) was treated separately with 325 μM of oligonucleotides 27 (SEQ ID NO:1 with 3'-Cy3), 28 (SEQ ID NO:1), 32 (SEQ ID NO:6), 50 (SEQ ID NO:5 with 3'-Cy3), and 61 (SEQ ID NO:7), each containing a hydrazide group at the 5' end (C6 I-link, Integrated DNA Technologies, Inc.) in 200 μL for 1 h at room temperature. Two μL of 5 M NaBH$_3$CN in 1M NaOH was added (final concentration 50 mM) and incubated at room temperature for 30 min. Unreacted aldehyde sites were then removed by the addition of 1 μL of 3 M ethanolamine, pH 7 (final concentration 15 mM) followed by 30 min incubation at room temperature. The laccase was then washed 3-times in an Amicon Ultra-4 (30,000 MWCO) (Millipore) with 100 mM Na Acetate pH 5.0. Total wash 8000-fold.

The resulting preparation was analyzed by SDS-polyacrylamide gel electrophoresis. Staining the protein bands with Coomassie Blue showed that the molecular mass of the laccase was increased by this treatment. Staining of parallel lanes on the same gel with ethydium bromide revealed that the same protein bands also contained oligonucleotides. Both indicated that the oligonucleotides were indeed attached to laccase. The enzymatic activity of the laccase/oligo adduct was assayed using the ABTS$^{-2}$ substrate and was shown in all cases to be ≧50% of the starting activity.

Inhibitor Linking to DNA

The 3,4-di-OH-2,6-di-Cl-benzaldehyde prepared above is coupled to Maleimide-dPEG$_4$-NHS ester (as shown in Diagram IV), followed by coupling to an oligonucleotide. Maleimide-dPEG$_4$-NHS-ester (Quanta Biodesign Inc.; Powell, Ohio) is derivatized with hydrazine to give the hydrazide. The product is reacted with 3,4-di-OH-2,6-diCl-benzaldehyde to give the hydrazone. This product is either used directly, or is reduced to the substituted hydrazide.

Diagram IV

Strategy for inhibitor coupling to 5'-hydrazide linked DNA thiolated at 3' end

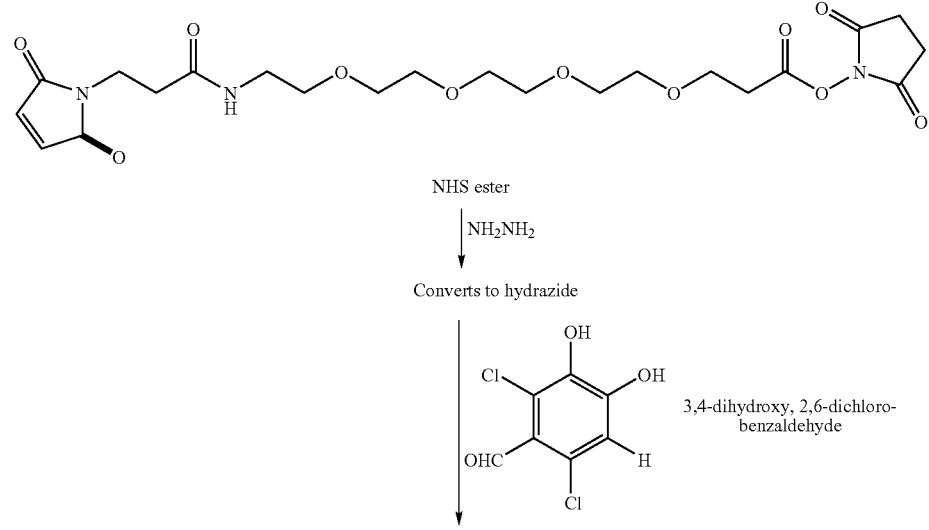

-continued

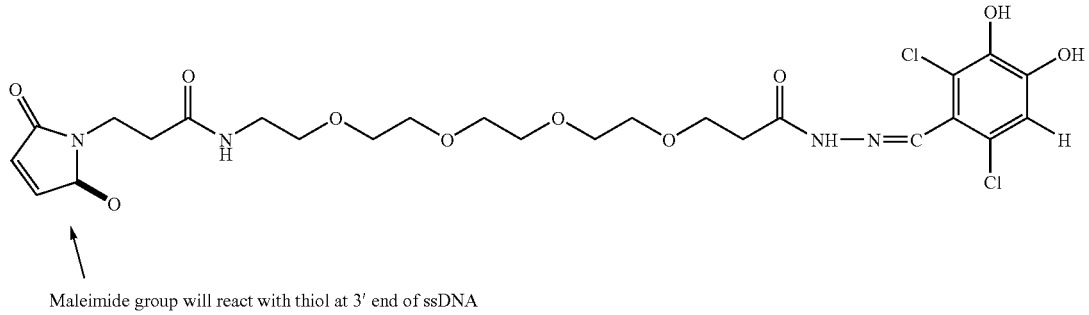

Maleimide group will react with thiol at 3' end of ssDNA

The maleimide group of the product is then coupled to the thiol group of a 5'-hydrazide, 3'-thiol coupled oligonucleotide. This product is then coupled through the hydrazide group to aldehydes of periodate-oxidized laccase, as described above.

Example 14

Polymer Stamp as Separate Capture Moiety Surface

The use of a polymer stamp in a carbon nanotube device is desirable since it allows the use of multiple polymer stamps with different attached DNA probes in the same carbon nanotube device, providing cost and time savings.

A bare polymer stamp is formed by filling a silicon, hard back photoresist master mold with a solution of PDMS (polydimethylsiloxane) and then curing it in an oven at about 80° C. The structure of the mold forms a 100 μm wide and 50 μm deep channel in the polymer stamp. After the polymer stamp is peeled away from the mold, it is processed chemically in order to modify the surface in the channel with molecules suitable for DNA attachment. A thin layer of $SiO_2$ is deposited onto the stamp channel surface in order to use the silane-based chemistry for DNA attachment as described in Examples 8 and 9. The polymer stamp is then incubated with a solution containing single stranded 3'-SANH-derivatized oligonucleotide probe molecules. Once attachment is complete, the stamp is washed with a buffer solution to remove unattached molecules. The polymer stamp is used in two different ways: (1) The polymer stamp is then placed on top of the carbon nanotube device and pressed against the surface of the chip to seal the channel against leakage. The channel is centered with respect to the sensing area of the device, so that a buffer solution can flow through the channel and over the carbon nanotubes. A solution containing the Laccase/oligonucleotide probe adduct described in Example 13 and the analyte DNA described in Example 9 is then pushed through the channel, and DNA hybridization to the surface-bound oligonucleotide probes is allowed to proceed. Unbound laccase is removed by washing and $ABTS^{-2}$ is added to begin the detection; or (2) before placing the polymer stamp on the chip, it is incubated in a solution of Laccase/oligonucleotide probe adduct and analyte DNA to allow hybridization to the surface-attached oligonucleotide probes. Unbound laccase is removed by washing. The polymer stamp is then centered and placed on top of the carbon nanotube device and pressed against its surface as above. The $ABTS^{-2}$ solution is then flowed into the channel for the detection of bound laccase. The latter approach has the advantage of hybridization taking place away from the CNT device making the test simple and easily repeatable, and allowing reuse of devices.

What is claimed is:

1. A nanosensor for detecting the presence of an analyte comprising:
   a) at least two electrodes connected by an electrically conducting path comprised of one or more carbon nanotubes wherein at least one of said carbon nanotubes is semiconducting and wherein the carbon nanotube is in contact with an effector solution having a redox potential;
   b) a capture moiety having affinity for an analyte and attached to a surface;
   c) a redox reporter conjugate comprising a redox reporter linked to an analyte receptor, said analyte receptor having affinity for the analyte; and
   d) a redox active substrate and a co-substrate.

2. A nanosensor according to claim 1 wherein the effector solution comprises a redox mediator.

3. A nanosensor according to claim 1 further comprising a gate electrode.

4. A nanosensor according to claim 1 wherein said surface is the surface of a nanotube.

5. A nanosensor according to claim 1 wherein said surface is the surface of a support.

6. A nanosensor according to claim 5 wherein said support is comprised of materials selected from the group consisting of silicon, silicon dioxide, silicon nitride, polysilicon, polymeric materials, glass, agarose, carbon, metals, ferromagnetic materials, nitrocellulose, nylon, insulating materials and semiconducting materials.

7. A nanosensor according to claim 5 wherein said support is in the form of a bead.

8. A nanosensor according to claim 5 wherein said support is in the form of a pad or stamp.

9. A nanosensor according to claim 8 wherein said stamp comprise a channel.

10. A nanosensor according to claim 1 wherein the capture moiety is a first member of a binding pair and the analyte is a second member of a binding pair.

11. A nanosensor according to claim 1 wherein the analyte receptor is a first member of a binding pair and the analyte is a second member of a binding pair.

12. A nanosensor according to claim 10 or 11 wherein the first and second members of a binding pair are members of binding pairs selected from the group consisting of antigen/epitope, receptor/ligand, binding protein/protein, nucleic acid binding polypeptide/nucleic acid, complementary nucleic acid single strands and peptide nucleic acid and complementary nucleic acid.

13. A nanosensor according to claim 1 wherein the carbon nanotube is supported on a support.

14. A nanosensor according to claim 13 wherein the support is comprised of materials selected from the group consisting of silicon, polysilicon, silicon dioxide, silicon nitride, polymeric materials, glass, agarose, nitrocellulose, nylon, and insulating materials.

15. A nanosensor according to claim 1 wherein the carbon nanotube is suspended between at least two electrodes.

16. A nanosensor according to claim 15 wherein the enzyme is selected from the group consisting of laccase, glucose oxidase, cholesterol oxidase, alcohol dehydrogenase, bilirubin oxidase, lactate dehydrogenase, and D-amino acid oxidase.

17. A nanosensor according to claim 1 wherein the redox potential of the effector affects the density of charge carriers on the carbon nanotube.

18. A nanosensor according to claim 1 wherein the redox reporter is an enzyme.

19. A nanosensor according to claim 1 wherein the redox active substrate and co-substrate are independently selected from the group consisting of ABTS, $O_2$, DCPIP, NAD (NADH), NADP (NADPH), flavin, o-, m- and p-quinones, glucose, cholesterol, bilirubin, alcohols, and D-amino acids.

20. A nanosensor according to claim 1 wherein the carbon nanotube is uncoated.

21. A nanosensor according to claim 1 wherein the carbon nanotube is substantially free of metal.

22. A method for detecting an analyte comprising:
   a) providing a nanosensor comprising:
      i) at least two electrodes connected by an electrically conducting path comprised of one or more carbon nanotubes wherein at least one of said carbon nanotubes is semiconducting, and wherein the carbon nanotube is in contact with an effector solution having a redox potential wherein the carbon nanotube has a baseline conductance;
      ii) a capture moiety having affinity for an analyte, the capture moiety attached to a surface; and
      iii) a redox reporter conjugate comprising an analyte receptor and a redox reporter;
   b) providing a sample suspected of containing an analyte;
   c) contacting the sample of (b) with the capture moiety of the nanosensor of (a) wherein the analyte present in the sample binds to the capture moiety and the analyte receptor of the redox reporter conjugate to form a capture-analyte-redox reporter complex;
   d) contacting the capture-analyte-redox reporter complex of step (c) with a redox active substrate and co-substrate wherein the redox potential of the effector solution is altered resulting in a change in the conductance of the carbon nanotube with respect to the baseline conductance; and
   e) measuring the change in the conductance of the carbon nanotube with respect to the baseline conductance whereby the presence of the analyte is detected.

23. A method according to claim 22 wherein the effector solution comprises a redox mediator.

24. A method according to claim 22 wherein the capture moiety is a first member of a binding pair and the analyte is a second member of a binding pair.

25. A method according to claim 22 wherein the analyte receptor is a first member of a binding pair and the analyte is a second member of a binding pair.

26. A method according to claim 24 or 25 wherein the first and second members of a binding pair are members of binding pairs selected from the group consisting of antigen/epitope, receptor/ligand, binding protein/protein, nucleic acid binding polypeptide/nucleic acid, complementary nucleic acid single strands, and peptide nucleic acid and complementary nucleic acid.

27. A method according to claim 22 wherein the redox potential of the effector affects the density of charge carriers in the CNT.

28. A method according to claim 22 wherein the redox effector is the redox active substrate, the redox active co-substrate or a redox mediator that is in equilibrium with either the substrate or the co-substrate.

29. A method according to claim 22 wherein said surface is comprised of materials selected from the group consisting of silicon, silicon dioxide, silicon nitride, polysilicon, polymeric materials, glass, agarose, carbon, metals, ferromagnetic materials, nitrocellulose, nylon, insulating materials and semiconducting materials.

30. A method according to claim 22 wherein the redox reporter is an enzyme.

31. A method according to claim 30 wherein the enzyme is selected from the group consisting of laccase, glucose oxidase, cholesterol oxidase, alcohol dehydrogenase, lactate dehydrogenase, and D-amino acid oxidase.

32. A method according to claim 22 wherein the redox active substrate is selected from the group consisting of ABTS, $O_2$, DCPIP, $NAD^+$(NADH), NADP (NADPH), flavin, o-, m- and p-quinones, glucose, cholesterol, alcohols, and D-amino acids.

33. A method according to claim 22 wherein the analyte is selected from the group consisting of a nucleic acid, a polypeptide, a virus, a cell, a metabolite and a product.

34. A nanosensor for the detection of an analyte comprising:
   a) at least two electrodes connected by an electrically conducting path comprised of one or more carbon nanotubes wherein at least one of said carbon nanotubes is semiconducting and wherein the carbon nanotube is in contact with an effector solution having a redox potential; and b) a means for altering said redox potential in response to the presence of an analyte.

35. A method for detecting the presence of an analyte comprising:
- a) providing a nanosensor comprising:
    - i) at least two electrodes connected by an electrically conducting path comprised of one or more carbon nanotubes wherein at least one of said carbon nanotubes is semiconducting and wherein the carbon nanotube is in contact with an effector solution having a redox potential and wherein the carbon nanotube has a baseline conductance; and
    - ii) a means for altering said redox potential in response to the presence of an analyte;
- b) contacting the nanosensor of (a) with an analyte whereby the effector redox potential is altered resulting in a change in the conductance of said carbon nanotube; and
- c) measuring the alteration in the conductance of the carbon nanotube of (b) wherein the presence of the analyte is detected.

* * * * *

UNITED STATES PATENT AND TRADEMARK OFFICE
CERTIFICATE OF CORRECTION

PATENT NO. : 7,635,423 B2 Page 1 of 1
APPLICATION NO. : 11/241515
DATED : December 22, 2009
INVENTOR(S) : Boussaad et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 946 days.

Signed and Sealed this

Ninth Day of November, 2010

David J. Kappos
*Director of the United States Patent and Trademark Office*

SEQUENCE LISTING

```
<160> NUMBER OF SEQ ID NOS: 7

<210> SEQ ID NO 1
<211> LENGTH: 18
<212> TYPE: DNA
<213> ORGANISM: artificial sequence
<220> FEATURE:
<223> OTHER INFORMATION: synthetic oligo

<400> SEQUENCE: 1
cgctgtgatg gtggcccc                                                 18

<210> SEQ ID NO 2
<211> LENGTH: 18
<212> TYPE: DNA
<213> ORGANISM: artificial sequence
<220> FEATURE:
<223> OTHER INFORMATION: synthetic oligo

<400> SEQUENCE: 2
```

```
ggggccacca tcacagcg                                                    18

<210> SEQ ID NO 3
<211> LENGTH: 28
<212> TYPE: DNA
<213> ORGANISM: artificial sequence
<220> FEATURE:
<223> OTHER INFORMATION: synthetic oligo

<400> SEQUENCE: 3
cgctgtgatg gtggcccctt tttttttt                                         28

<210> SEQ ID NO 4
<211> LENGTH: 46
<212> TYPE: DNA
<213> ORGANISM: artificial sequence
<220> FEATURE:
<223> OTHER INFORMATION: synthetic oligo

<400> SEQUENCE: 4
ggggccacca tcacagcgtt tttttttgg ggccaccatc acagcg                      46

<210> SEQ ID NO 5
<211> LENGTH: 18
<212> TYPE: DNA
<213> ORGANISM: artificial sequence
<220> FEATURE:
<223> OTHER INFORMATION: synthetic oligo

<400> SEQUENCE: 5
cgctgtgatg gtggcccc                                                    18

<210> SEQ ID NO 6
<211> LENGTH: 28
<212> TYPE: DNA
<213> ORGANISM: artificial sequence
<220> FEATURE:
<223> OTHER INFORMATION: synthetic oligo

<400> SEQUENCE: 6
tttttttttt cgctgtgatg gtggcccc                                         28

<210> SEQ ID NO 7
<211> LENGTH: 36
<212> TYPE: DNA
<213> ORGANISM: artificial sequence
<220> FEATURE:
<223> OTHER INFORMATION: synthetic oligo

<400> SEQUENCE: 7
tttttttttt ttttcctcgt cagatttgtc cttgca                                36
```